United States Patent
Khalil et al.

(10) Patent No.: US 7,043,287 B1
(45) Date of Patent: May 9, 2006

(54) METHOD FOR MODULATING LIGHT PENETRATION DEPTH IN TISSUE AND DIAGNOSTIC APPLICATIONS USING SAME

(75) Inventors: Omar S. Khalil, Libertyville, IL (US); Shu-Jen Yeh, Grayslake, IL (US); Xiaomao Wu, Gurnee, IL (US); Stanislaw Kantor, Buffalo Grove, IL (US); Charles F. Hanna, Libertyville, IL (US); Tzyy-Wen Jeng, Vernon Hills, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/419,461

(22) Filed: Oct. 15, 1999

Related U.S. Application Data

(63) Continuation-in-part of application No. 09/302,207, filed on Apr. 29, 1999, now Pat. No. 6,241,663, which is a continuation-in-part of application No. 09/080,470, filed on May 18, 1998, now Pat. No. 6,662,030.

(51) Int. Cl.
*A61B 5/00* (2006.01)

(52) U.S. Cl. ........................................ 600/310; 600/316

(58) Field of Classification Search ........ 600/310–311, 600/316, 322–324, 326, 328, 334, 339; 356/39–41
See application file for complete search history.

(56) References Cited

U.S. PATENT DOCUMENTS

| | | |
|---|---|---|
| 3,628,525 A | 12/1971 | Polanyi et al. |
| 3,638,640 A | 2/1972 | Shaw |
| 4,223,680 A | 9/1980 | Jobsis |
| 4,259,963 A | 4/1981 | Huch |
| 4,432,365 A | 2/1984 | Leist |
| 4,655,225 A | 4/1987 | Dahne et al. |
| 4,882,492 A | 11/1989 | Schlager |
| 4,890,619 A | 1/1990 | Hatschek |
| 4,926,867 A | 5/1990 | Kanda et al. |
| 4,975,581 A | 12/1990 | Robinson et al. |
| 5,007,423 A | 4/1991 | Branstetter et al. |
| 5,057,695 A | 10/1991 | Hirao et al. |
| 5,086,229 A | 2/1992 | Rosenthal et al. |
| 5,115,133 A | 5/1992 | Knudson |
| 5,122,974 A | 6/1992 | Chance |
| 5,131,391 A | 7/1992 | Sakai et al. |
| 5,148,082 A | 9/1992 | Itou et al. |
| 5,187,672 A | 2/1993 | Chance et al. |
| 5,209,231 A | 5/1993 | Cote et al. |
| 5,218,207 A | 6/1993 | Rosenthal |
| 5,237,178 A | 8/1993 | Rosenthal et al. |
| 5,277,181 A | 1/1994 | Mendelson et al. |
| 5,284,139 A | 2/1994 | Khalil et al. |
| 5,297,548 A | 3/1994 | Pologe |
| 5,313,941 A | 5/1994 | Braig et al. |
| 5,321,265 A | 6/1994 | Block |
| 5,324,979 A | 6/1994 | Rosenthal |
| 5,337,745 A | 8/1994 | Benaron |
| 5,348,002 A | 9/1994 | Caro |
| 5,348,003 A | 9/1994 | Caro |
| 5,361,758 A | 11/1994 | Hall et al. |
| 5,362,966 A | 11/1994 | Rosenthal et al. |
| 5,372,136 A | 12/1994 | Steuer et al. |
| 5,379,764 A | 1/1995 | Barnes et al. |
| 5,383,452 A | 1/1995 | Buchert |
| 5,402,778 A | 4/1995 | Chance |
| 5,452,716 A | 9/1995 | Clift |
| 5,481,113 A | 1/1996 | Dou et al. |
| 5,492,118 A | 2/1996 | Gratton et al. |
| 5,492,769 A | 2/1996 | Pryor et al. |
| 5,497,769 A * | 3/1996 | Gratton et al. .............. 600/323 |
| 5,499,627 A | 3/1996 | Steuer et al. |
| 5,515,847 A | 5/1996 | Braig et al. |
| 5,533,509 A | 7/1996 | Koashi et al. |
| 5,551,422 A | 9/1996 | Simonsen et al. |
| 5,553,615 A | 9/1996 | Carim et al. |
| 5,553,616 A | 9/1996 | Ham et al. |
| 5,596,987 A | 1/1997 | Chance |
| 5,665,530 A | 9/1997 | Oyamada et al. |
| 5,672,875 A | 9/1997 | Block et al. |
| 5,676,143 A | 10/1997 | Simonsen et al. |
| 5,720,284 A | 2/1998 | Aoyagi et al. |
| 5,725,480 A | 3/1998 | Oosta et al. |
| 5,755,226 A | 5/1998 | Carim et al. |

$T_1 > T_2 > T_3$

| | | | |
|---|---|---|---|
| 5,770,454 A | | 6/1998 | Essenpris et al. |
| 5,782,755 A | * | 7/1998 | Chance et al. ............... 600/322 |
| 5,823,951 A | | 10/1998 | Messerschmidt |
| 5,873,821 A | * | 2/1999 | Chance et al. ............... 600/310 |
| 5,931,779 A | * | 8/1999 | Arakaki et al. ............. 600/310 |
| 5,978,691 A | * | 11/1999 | Mills .......................... 600/334 |
| 6,161,028 A | * | 12/2000 | Braig et al. .................. 600/316 |
| 6,198,949 B1 | * | 3/2001 | Braig et al. .................. 600/310 |

FOREIGN PATENT DOCUMENTS

| | | |
|---|---|---|
| DE | 44 17 639 | 11/1995 |
| DE | 196 34 152 | 3/1998 |
| EP | 0 472 216 | 2/1992 |
| EP | 0 810 429 | 12/1997 |
| WO | 92/10131 | 6/1992 |
| WO | 93/20273 | 11/1992 |
| WO | 93/07801 | 4/1993 |
| WO | 93/13706 | 7/1993 |
| WO | 94/02837 | 2/1994 |
| WO | 94/05984 | 3/1994 |
| WO | 94/13199 | 6/1994 |
| WO | 95/20757 | 8/1995 |
| WO | 98/03847 | 1/1998 |
| WO | 99/39631 | 8/1999 |
| WO | 99/55222 | 11/1999 |
| WO | 99/59464 | 11/1999 |

OTHER PUBLICATIONS

Applied Optics, vol. 31, No. 10, Apr. 1, 1992.
Bruulsema, et al., "Correlation between blood glucose concentration in diabetics and noninvasively measured tissue optical scattering coefficient", Optics Letters, vol. 22, No. 3, 1997, pp. 190-192.
Heinemann, et al., "Non-invasive continuous glucose monitoring in Type 1 diabetic patients with optical glucose sensors", Diabetologia, vol. 41, 1998, pp. 848-854.
Kienle, et al. "Spatially resolved absolute diffuse reflectance measurements for noninvasive determination of the optical scattering and absorption coefficients of biological tissue", Applied Optics, vol. 35, No. 13, 1996, pp. 2304-214.
Marbach, et al., "Noninvasive Blood Glucose Assay by Near-Infrared Diffuse Reflectance Spectroscopy of the Human Inner Lip", Applied Spectroscopy, vol. 47, No. 7, 1993, pp. 875-881.
Qu, et al., "Monte Carlo Modeling Studies of the Effect of Physiological Factors and other Analytes on the Determination of Glucose Concentration In vivo by Near Infrared Optical Absorption and Scattering Measurements", Journal of Biomedical Optics, vol. 2, No. 3, (1997), pp. 319-325.
Quan, et al., "Glucose determination by a pulsed photoacoustic technique: an experimental study using a gelatin-based tissue phantom", Phys. Med. Biol., vol. 38 (1993) pp. 1911-1922.
Robbins, et al., "The Endocrine Pancreas", Pathologic Basis of Disease, 3rd Edition, W. B. Saunders Company (1984), pp. 972-990.
Tooke, et al., "Skin Microvascular Blood Flow Control in Long Duration Diabetics with an without Complications", Diabetes Research, No. 5, 1987, pp. 189-192.
Wilson, et al, "Progress toward the Development of an Implantable Sensor for Glucose", Clinical Chemistry, vol. 38, No. 9, 1992, pp. 1613-1617.
R. Graaff, et al., "Reduced light-scattered properties for mixtures of spherical particles: a simple approximation derived from Mie calculations", Applied Optics, vol. 31, No. 10, Apr. 1, 1992, pp. 1370-1376.

Jobsis, "Noninvasive, Infrared Monitoring of Cerebral and Myocardial Oxygen Sufficiency and Circulatory Parameters", Science, vol. 198, 1977, pp. 1264-1267.
Gopinath, et al., "Near-infrared spectroscopic localization of intracranial hematomas", Journal of Neurosurgery, vol. 79. 1993, pp. 43-47.
Zhang, et al., "Investigation of Noninvasive in Vivo Blood Hematocrit Measurement Using NIR Reflectance Spectroscopy and Partial Least-Squares Regression", Applied Spectroscopy, vol. 54, No. 2, 2000, pp. 294-299.
Lin, et al., "Dynamics of tissue optics during laser heating of turbid media", Applied Optics, vol. 35, No. 19, 1996, pp. 3413-3420.
Laufer, et al., "Effect of temperature on the optical properties of ex vivo human dermis and subdermis", Phys. Med. Biol., vol. 43, 1998, pp. 2479-2489.
Bruulsema, et al., "Optical Properties of Phantoms and Tissue Measured in vivo from 0.9-13 μm using Spatially Resolved Diffuse Reflectance", SPIE Proceedings, vol. 2979, 1997, pp. 325-334.
T. Shiga, et al., "Study of an Algorithm Based on Model Experiments and Diffusion Theory for a Portable Tissue Oximeter", Journal of Biomedical Optics, vol. 2, No. 2, Apr. 1997, pp. 154-161.
Jacques, et al., "Monte Carlo Modeling of Light Transport in Tissues", Optical-Thermal Response of Laser-Irradiated Tissue, edited by A.J. Welch and M.J.C. van Gemert, Plenum Press, New York, 1995, pp. 73-100.
Wilson, "Measurement of Tissue Optical Properties: Methods and Theories", Optical-Thermal Response of Laser-Irradiated Tissue, edited by A.J. Welch and M.J.C. van Gemert, Plenum Press, New York, 1995, pp. 233-274.
Morris, et al., "Basic Examination of Blood", Clinical Diagnosis and Management by Laboratory, 1996, pp. 549-559.
Lin, et al., "Dynamics of tissue reflectance and transmittance during laser irradiation", SPIE Proceedings, vol. 2134A Laser-Tissue Interaction V, 1994, pp. 296-303.
PCT International Search Report.

* cited by examiner

Primary Examiner—Eric F. Winakur
(74) Attorney, Agent, or Firm—David L. Weinstein

(57) ABSTRACT

Devices and methods for non-invasively measuring at least one parameter of a sample, such as the presence of a disease condition, progression of a disease state, presence of an analyte, or concentration of an analyte, in a biological sample, such as, for example, a body part. In these devices and methods, temperature is controlled and is varied between preset boundaries. The methods and devices measure light that is reflected, scattered, absorbed, or emitted by the sample from an average sampling depth, $d_{av}$, that is confined within a region in the sample wherein temperature is controlled. According to the method of this invention, the sampling depth $d_{av}$, in human tissue is modified by changing the temperature of the tissue. The sampling depth increases as the temperature is lowered below the body core temperature and decreases when the temperature is raised within or above the body core temperature. Changing the temperature at the measurement site changes the light penetration depth in tissue and hence $d_{av}$. Change in light penetration in tissue as a function of temperature can be used to estimate the presence of a disease condition, progression of a disease state, presence of an analyte, or concentration of an analyte in a biological sample. According to the method of this invention, an optical measurement is performed on a biological sample at a first temperature. Then, when the optical measurement is repeated at a second temperature, light will penetrate into the biological sample to a depth that is different from the depth to which light penetrates at the first temperature by from about 5% to about 20%.

30 Claims, 14 Drawing Sheets

METHOD FOR MODULATING LIGHT PENETRATION DEPTH IN TISSUE AND DIAGNOSTIC APPLICATIONS USING SAME

This invention is a continuation-in-part of U.S. Ser. No. 09/080,470, filed May 18, 1998, now U.S. Pat. No. 6,662,030, and is a continuation-in-part of U.S. Ser. No. 09/302,207, filed Apr. 29, 1999, now U.S. Pat. No. 6,241,663.

BACKGROUND OF THE INVENTION

1. Field of the Invention

This invention relates to devices and methods for the noninvasive determination of in vivo concentrations of analytes or evaluation of a disease state, and more particularly, the noninvasive determination of in vivo concentrations of analytes or evaluation of a disease state wherein temperature is controlled and varied between preset boundaries.

2. Discussion of the Art

Non-invasive monitoring of concentrations of analytes in the human body by means of optical devices and optical methods is an important tool for clinical diagnosis. "Non-invasive" (alternatively referred to herein as "NI") monitoring techniques measure in vivo concentrations of analytes in the blood or in the tissue without the need for obtaining a blood sample from the human body. As used herein, a "non-invasive" technique is one that can be used without removing a sample from, or without inserting any instrumentation into, the human body. The ability to determine the concentration of an analyte, or a disease state, in a human subject without performing an invasive procedure, such as removing a sample of blood or a biopsy specimen, has several advantages. These advantages include ease in performing the test, reduced pain and discomfort to the patient, and decreased exposure to potential biohazards. These advantages tend to promote increased frequency of testing, accurate monitoring and control of a disease condition, and improved patient care. Representative examples of non-invasive monitoring techniques include pulse oximetry for oxygen saturation (U.S. Pat. Nos. 3,638,640; 4,223,680; 5,007,423; 5,277,181; and 5,297,548). Another example of a non-invasive monitoring technique is the use of laser Doppler flowmetry for diagnosis of circulation disorders (J. E. Tooke et al., "Skin Microvascular Blood Flow Control in Long Duration Diabetics With and Without Complications", Diabetes Research (1987) 5, 189–192). Other examples of NI techniques include determination of tissue oxygenation (WO 92/20273), determination of hemoglobin (U.S. Pat. No. 5,720,284), and determination of hematocrit (U.S. Pat. Nos. 5,553,615; 5,372,136; 5,499,627; and WO 93/13706). Determination of bilirubin was also described in the art (R. E. Schumacher, "Noninvasive Measurements of Bilirubin in the Newborn", Clinics in Perinatology, Vol. 17, No. 2 (1990) 417–435, and U.S. Pat. No. 5,353,790).

Non-invasive diagnosis and monitoring of diabetes may be the most important non-invasive diagnostic procedure. Diabetes mellitus is a chronic disorder of carbohydrate, fat, and protein metabolism characterized by an absolute or relative insulin deficiency, hyperglycemia, and glycosuria. At least two major variants of the disease have been identified. "Type I" accounts for about 10% of diabetics and is characterized by a severe insulin deficiency resulting from a loss of insulin-secreting beta cells in the pancreas. The remainder of diabetic patients suffer from "Type II", which is characterized by an impaired insulin response in the peripheral tissues (Robbins, S. L. et al., *Pathologic Basis of Disease*, 3$^{rd}$ Edition, W.B. Saunders Company, Philadelphia, 1984, p. 972). If uncontrolled, diabetes can result in a variety of adverse clinical manifestations, including retinopathy, atherosclerosis, microangiopathy, nephropathy, and neuropathy. In its advanced stages, diabetes can cause blindness, coma, and ultimately death.

Non-invasive determination of glucose has been the subject of several patents. U.S. Pat. Nos. 5,082,787; 5,009,230; 4,975,581; 5,379,764; 4,655,225; 5,551,422; 5,893,364; 5,497,769; 5,492,118; 5,209,231; and 5,348,003 describe a variety of optical methods for the noninvasive determination of glucose in the human body. However, all the previously mentioned patents are silent as to the effect of different layers of skin on optical measurements, or the effect of temperature on light penetration through these various layers of the skin. U.S. Pat. No. 5,935,062 recognizes the presence of skin layers and describes means to detect diffusely reflected light from the dermis and avoid light interacting with the epidermis by using a black barrier on the skin to separate specular reflectance and reflectance from the epidermis from reflected light that penetrated to the dermis. However, U.S. Pat. No. 5,935,062 is silent as to the effect of temperature on light penetrating through these layers of skin. The effect of temperature on the scattering and absorption properties of tissue has been of interest in the art. Thermal effects of laser excitation, photocoagulation, and temperature effect on skin optics have been described in the art. See, for example, W-C. Lin et al., "Dynamics of tissue reflectance and transmittance during laser irradiation", SPIE Proceedings, 2134A Laser-Tissue Interaction V (1994) 296–303; and W—C. Lin, "Dynamics of tissue optics during laser heating of turbid media", Applied Optics (1996) Vol. 35, No. 19, 3413–3420; J. Laufer et al., "Effect of temperature on the optical properties of ex vivo human dermis and subdermis", Phys. Med. Biol. 43 (1998) 2479–2489; J. T. Bruulsema et al., "Optical Properties of Phantoms and Tissue Measured in vivo from 0.9–1.3 µm using Spatially Resolved Diffuse Reflectance", SPIE Proceedings 2979 (1997) 325–334.

U.S. Pat. Nos. 3,628,525; 4,259,963; 4,432,365; 4,890,619; 4,926,867; 5,131,391; and European Patent Application EP 0472216 describe oximetry probes having heating elements designed to be placed against a body part. U.S. Pat. No. 5,148,082 describes a method for increasing the blood flow in a patient's tissue, during a photoplethsmography measurement, by heating the tissue with a semiconductor device mounted in a sensor. U.S. Pat. No. 5,551,422 describes a glucose sensor that is brought to a specified temperature, preferably somewhat above normal body temperature, with a thermostatically controlled heating system.

U.S. application Ser. No. 09/080,470, filed May 18, 1998, assigned to the assignee of this application, describes a non-invasive glucose sensor employing a temperature control. One purpose of controlling the temperature is to minimize the effect of physiological variables. U.S. application Ser. No. 09/098,049, filed Nov. 23, 1998, assigned to the assignee of this application, describes methods for determining optical properties of tissue having a plurality of layers. Both applications teach the use of temperature controlled optical element that is brought in contact with the skin.

Although a variety of detection techniques have been disclosed in the art, there is still no commercially available device that provides non-invasive glucose measurements with an accuracy that is comparable to the current commercially available invasive devices. Signals obtained by prior art methods reflect the analyte information of the tissue as if the tissue comprised a single uniform layer that has a single uniform temperature. As a result, current approaches to non-invasive metabolite testing, such as glucose monitoring, have not achieved acceptable precision and accuracy.

Thus, there is a continuing need for improved NI instruments and methods that are unaffected by variations in skin structures and layers or account for the effect of skin layers and the effect of temperature on the optical properties of these layers.

SUMMARY OF THE INVENTION

This invention provides devices and methods for non-invasively measuring at least one parameter of a sample, such as the presence of a disease condition, progression of a disease state, presence of an analyte, or concentration of an analyte, in a biological sample, such as, for example, a body part. In these devices and methods, temperature is controlled and is varied between preset boundaries.

The methods and devices of the present invention measure light that is reflected, scattered, absorbed, or emitted by the sample from an average sampling depth, $d_{av}$, that is confined within a region in the sample wherein temperature is controlled. According to the method of this invention, the sampling depth $d_{av}$, in human tissue is modified by changing the temperature of the tissue. The sampling depth increases as the temperature is lowered below the body core temperature and decreases when the temperature is raised within or above the body core temperature. As used herein, the phrase "body core temperature" means the temperature of the interior of the body remote from the extremities of the body. Rectal temperature and esophageal temperature represent body core temperature. For normal human beings, body core temperature is $37\pm1°$ C. Changing the temperature at the measurement site changes the light penetration depth in tissue and hence $d_{av}$. Change in light penetration in tissue as a function of temperature can be used to estimate the presence of a disease condition, progression of a disease state, presence of an analyte, or concentration of an analyte in a biological sample. According to the method of this invention, an optical measurement is performed on a biological sample at a first temperature. Then, when the optical measurement is repeated at a second temperature, light will penetrate into the biological sample to a depth that is different from the depth to which light penetrates at the first temperature by from about 5% to about 20%.

It is possible to limit the sampling depth in the tissue by appropriate selection of the separation between the light introduction site and the light collection site (the sampling distance). The sampling depth also varies at different wavelengths of light, the sampling depth being greater at longer wavelengths, in the range of about 500 nm to about 1300 nm. For human skin with light pigmentation, the sampling depth ranges from 200 μm at wavelengths below 500 nm, reaches 1 mm at a wavelength of 600 nm, and increases further to 2 mm at wavelengths ranging from about 700 nm to about 1100 nm.

In one aspect, the present invention provides an improved method of measuring at least one parameter of a biological sample comprising the steps of:
 (a) setting the temperature of the biological sample to a first temperature, the first temperature being within the physiological temperature range of the biological sample;
 (b) performing an optical measurement on the biological sample at the first temperature;
 (c) determining at least one optical parameter of the biological sample at the first temperature, the first temperature corresponding to a first depth in the biological sample;
 (d) changing the first temperature of the biological sample to at least a second temperature, the at least second temperature being within the physiological temperature range of the biological sample;
 (e) performing an optical measurement on the biological sample at the at least second temperature;
 (f) determining the at least one optical parameter of the biological sample at the at least second temperature, the at least second temperature corresponding to a second depth in the biological sample; and
 (g) determining the at least one parameter of the biological sample from the functional dependence of the at least one optical parameter on depth in the biological sample.

Parameters of biological samples include, but are not limited to, the presence of a disease condition, the progression of a disease state, the presence of an analyte, or the concentration of an analyte.

In another aspect, the present invention provides a method of measuring at least one parameter of a biological sample having a plurality of layers, the method comprising the steps of:
 (a) setting the temperature of the biological sample to a first temperature, the first temperature being within the physiological temperature range of the biological sample;
 (b) performing an optical measurement on the biological sample at the first temperature;
 (c) determining at least one optical parameter of a first layer of the biological sample, the first layer being located at a first depth of the biological sample, the first temperature corresponding to a first depth in the biological sample;
 (d) changing the temperature of the biological sample to at least a second temperature, the at least second temperature being within the physiological temperature range of the biological sample;
 (e) performing an optical measurement on the biological sample at the at least second temperature;
 (f) determining the at least one optical parameter at at least a second layer of the biological sample, the at least second layer being located at at least a second depth of the biological sample, the at least second temperature corresponding to the second depth of the biological sample; and
 (g) determining the at least one parameter of the biological sample from the functional dependence of the at least one optical parameter on depth in the biological sample.

The method of this invention can be used to determine a disease state or screen a population of individuals for a disease state.

In the preferred embodiments, radiation, i.e., light, is introduced into the surface of a biological sample, such as a body part, at a light introduction site. The diffusely reflected light collected at one or more light collection sites located on the surface of the sample at different distances, r, from the light introduction site is measured. For a given light collection site at a specific distance r from the light introduction site (sampling distance), the average light penetration depth in the biological sample varies with temperature. Light penetrates deeper into the biological sample as temperature is lowered below the body core temperature.

This invention involves increasing the penetration depth of radiation, i.e., light, into a biological sample by decreasing the temperature of the biological sample below the body core temperature (37±1° C.), while keeping the wavelength and the separation between the light introduction site and the light collection site (sampling distance) constant. The reduced scattering coefficient $\mu_s'$, measured in the near infrared region of the electromagnetic spectrum, changes instantaneously and reversibly when the temperature of the biological sample changes. The absorption coefficient $\mu_a$ changes instantaneously but with less regularity than the scattering coefficient, as temperature of the biological sample changes.

In another aspect, this invention provides an apparatus for determination of at least one parameter of a biological sample. The apparatus comprises:

(a) a means for irradiating a region of the biological sample with light;

(b) a means for collecting light re-emitted from the region of the biological sample, (c) a means for changing the temperature of the biological sample to a temperature within the physiological range of the biological sample so that radiation penetrates to a specified depth in the biological sample, (d) a means for measuring the intensity of the collected re-emitted light at a plurality of temperatures, wherein the measured intensities correspond to light re-emitted from different depths of the biological sample; and (e) a means for calculating at least one parameter of the biological sample from the dependence of at least one optical parameter on depth in the biological sample.

This invention provides advantages over techniques that use a spatially resolved diffuse reflectance measurement (e.g., U.S. Pat. Nos. 5,075,695; 5,492,118; and 5,551,422) in several respects. The method of this invention allows measuring changes in optical properties of a small volume of a biological sample along the light propagation path, perpendicular to the surface of the sample. These changes are measured by using small sampling distances, controlling the temperature range of the biological sample at the measurement site, and varying the temperature within the physiological temperature range. The method of this invention is preferable to prior art methods that use large sampling distances. These prior art methods are silent as to the effect of temperature on tissue optical properties. The method of this invention avoids skin surface irregularities and major tissue structural homogeneities as it detects only changes in optical properties at different depths while keeping the sampling distance and wavelengths of light constant.

The method of this invention is preferable to prior art methods for the determination of diabetic status (using blood glucose concentration as an index) that rely on changes in the scattering coefficient only. The method of this invention accounts for cutaneous vascular changes and blood flow changes, which are affected by diabetic status. The prior art is silent as to cutaneous vascular changes and blood flow changes in diabetic patients.

The method of this invention is preferable to prior art methods for the determination of diabetic status and other disease conditions based on measurement of body analytes in that the method relies on two measurements performed at the same site on the surface of the biological sample, thereby decreasing the effect of repositioning error and the possibility of the optical probe being in contact with different micro-structural regions of the biological sample during different single measurements.

The method of this invention is preferable to prior art methods that measure absorption at longer wavelengths in the near infrared region of the electromagnetic spectrum to determine glucose concentration, because those methods ignore scattering changes in biological sample, cutaneous blood flow, and cutaneous vascular structural changes in diabetic patients.

According to theories of light propagation in biological samples, light penetration depth in a biological sample depends on both the values of the absorption and scattering coefficients of the biological sample. Changing the temperature of the biological sample causes change in these optical parameters, and hence, change in light penetration depth, up to several hundred micrometers. This feature offers the ability to detect signals from closely spaced layers of a biological sample.

Change in light penetration depth in biological samples as a function of temperature has diagnostic applications. The change in light penetration depth can be used for diagnosing certain disease states that affect cutaneous structure, cutaneous vascular structure, and cutaneous blood flow. Diabetes, diabetic neuropathy, and peripheral vascular disease are examples of disease states that can be diagnosed by the method of this invention.

DETAILED DESCRIPTION OF THE INVENTION

Figure 1:
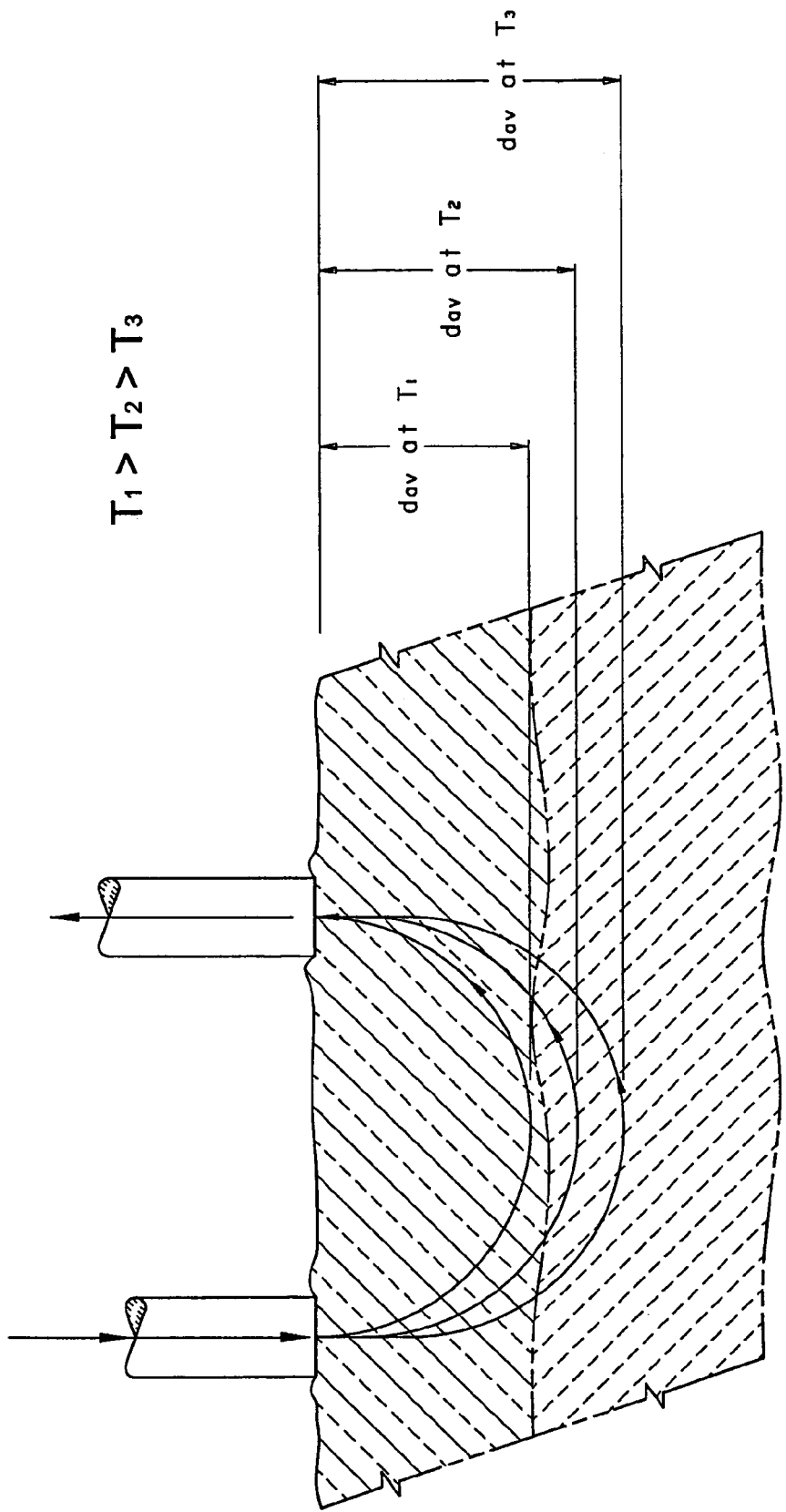
FIG. 1 illustrates light penetration in tissue at different temperatures.

As used herein, the expression "biological sample" includes, but is not limited to, a sample of intact or excised human tissue, such as, for example, a sample of intact or excised human skin, a human body part. The expression "tissue optics" refers to the study of light propagation in biological tissues. The expression "optical properties" refers to the absorption, scattering, emission, reflectance, and depolarization properties of the tissues.

The expression "optical parameter" refers to a parameter that describes and defines an optical property of a medium and its components. Examples of optical parameters include, but are not limited to, absorption coefficient, scattering coefficient, anisotropy factor, transport optical mean free path, and extinction coefficient of analytes. The expression "scattering media" refers to media that both scatter light and absorb light. The expression "absorption coefficient" (i.e., $\mu_a$) refers to the probability of light absorption per unit path length. The expression "scattering coefficient" (i.e., $\mu_s$) refers to the probability of light scattering per unit path length. The expression "anisotropy factor" (i.e., g) refers to the average cosine of the scattering angle for a multiply scattered photon. The expression "reduced scattering coefficient" (i.e., $\mu_s'$) refers to the probability of equivalently isotropic (uniform in all directions) scattering per unit path length. The reduced scattering coefficient is related to the scattering coefficient $\mu_s$ and the anisotropy factor g by the relationship $\mu_s'=(1-g)\mu_s$. The expression "light penetration depth" (i.e., $\delta$) refers to the rate of decay of light intensity in scattering media with respect to the path traveled by the light in the same direction as the incident light. Light penetration depth represents the depth at which light intensity in the tissue is attenuated to 1/e of its original value. The effective attenuation coefficient $\mu_{eff}$ is the reciprocal of the light penetration depth $\delta$, i.e., $\delta=1/\mu_{eff}$. As described in this application, light penetration depth in human skin is modified by changing the temperature at the measurement site, it increases as the temperature is lowered below the body core temperature.

The expression "Monte Carlo simulation" refers to a numerical method that can be used to statistically describe photon propagation in scattering media. The expression "diffuse reflectance" (reflectance therein unless specified otherwise) refers to measurement of light that is re-emitted from a sample at all angles different from the direction of the incident light, and over an area wider than the area where the incident light is introduced into the sample. The expressions "spatially resolved scattering" or "spatially resolved diffuse reflectance" refer to a measurement of light that is re-emitted from a sample and collected at several light collection sites at specific distances from a light introduction site. Alternatively, these expressions can refer to the light collected at a given light collection site on the sample boundary as a result of introducing light at discrete light introduction sites located on the same boundary at a set of defined distances from the light collection site. In both instances, $\mu_{eff}$, $\mu_a$ and $\mu_s'$ are calculated from the intensity distribution of the re-emitted light with respect to distances, i.e., the re-emitted light intensity at a multiplicity of sampling distances. The expressions "re-emitted light" and "reflected light" are used synonymously herein, as are the expressions "reflectance" and the "intensity of re-emitted light", unless otherwise indicated. The expression "frequency domain measurement" refers to a measurement of light involving the phase angle and/or the amplitude change of modulated incident light, at a given separation distance of a light introduction site from a light collection site, as the light transverses a scattering medium. The expression "beam of light" refers to a group of photons traveling together in nearly parallel trajectories toward a sample and striking the surface of the sample in a predefined area only. As a practical matter, the predefined area on the surface of a sample struck by a given beam of light is that area that is covered by an illuminating element, such as an optical fiber.

The expression "significantly affect" refers to a measurable effect in an optical property of a biological sample at a given depth in that biological sample resulting from a change in concentration of an analyte at that depth.

The expression "light introduction site" means a location on the surface of a sample, e.g., a body part, tissue, or the like, at which light is injected or introduced into the sample. The source of the light can be located at the light introduction site or can be located remote from the light introduction site. If the source of light is located remote from the light introduction site, the light must be transmitted to the light introduction site by light transmitting means, such as, for example, optical fibers. The expression "illuminating element" means a component located at the light introduction site that delivers light to the sample, e.g., a body part, tissue, or the like. The illuminating element is typically an optical fiber that transmits light from a source of light to the light introduction site. However, if the source of light is located at the light introduction site, the source of light can be the illuminating element. The expression "light collection site" means a location on the surface of a sample, e.g., a body part, tissue, or the like, at which light that is re-emitted from the sample is collected for measurement. The detector, which determines the intensity of the re-emitted light, can be located at the light collection site or can be located remote from the light collection site. If the detector is located remote from the light collection site, the light must be transmitted to the detector by light transmitting means, such as, for example, optical fibers. The expression "light collecting element" means a component located at the light collection site that collects light that is re-emitted from the sample, e.g., a body part, tissue, or the like. The light collecting element is typically an optical fiber that transmits light from the light collection site to a detector. However, if the detector can be located at the light collection site, the detector can be the light collecting element. The distance between a light introduction site and a light collection site, as measured along the surface of a sample, is defined as the "sampling distance". For a given sample, the sampling distance determines the mean distance from the surface of the sample into the interior of the sample at which the scattering and absorption events contribute to the measured re-emitted light. Such mean distance is hereinafter referred to as the "sampling depth", or "depth", which is dependent on the sampling distance. According to this invention the sampling depth in human skin is modified by changing the temperature of the tissue, it increases as the temperature is lowered within the body physiological temperature range.

As used herein, the expression "physiological temperature range" of a biological sample means the temperature range over which the biological activity of the sample is maintained, without irreversible change in the its optical or biological properties as a result of changing temperature.

In one aspect, the present invention provides an improved method of measuring at least one parameter of a biological sample comprising the steps of:

(a) setting the temperature of the biological sample to a first temperature, the first temperature being within the physiological temperature range of the sample;

(b) performing an optical measurement on the biological sample at the first temperature;

(c) determining at least one optical parameter of the biological sample at the first temperature, the first temperature corresponding to a first depth in the biological sample;

(d) changing the first temperature of the biological sample to at least to a second temperature, the at least second temperature being within the physiological temperature range of the biological sample;

(e) performing an optical measurement on the biological sample at the at least second temperature;

(f) determining the at least one optical parameter of the biological sample at the at least second temperature, the at least second temperature corresponding to a second depth in the biological sample; and (g) determining the at least one parameter of the biological sample from the functional dependence of the at least one optical parameter on depth in the biological sample.

In another aspect, this invention provides a method of measuring at least one parameter of a biological sample having a plurality of layers. Changes in light penetration depth as temperature is changed allows detecting light re-emitted from different layers, instead of detecting light re-emitted from different depths in a homogeneous sample as discussed in a previous paragraph. Typical skin tissue of a human body has at least three identifiable layers of tissue in the skin—the epidermis, the dermis, and subcutaneous tissue (Source: *Dorland's Illustrated Medical Dictionary*, 26$^{th}$ Ed., W.B. Saunders, Philadelphia, 1985, p. 1212). The epidermis is the outermost and nonvascular layer of the skin, varying in thickness from 70 to 120 µm, except on the palms and soles where it may be as thick as 0.8 mm and 1.4 mm, respectively. The epidermis can be further divided into layers. The dermis consists of a dense bed of vascular connecting tissue, typically varying in thickness from 1 to 2 mm. Although it contains venous plexus in both upper and lower layers, more adipose (i.e., fatty) tissues are found in the lower layer. Major veins are located in subcutaneous tissue.

The embodiment of the method involving a biological sample having a plurality of layers comprises the steps of:

(a) setting the temperature of the biological sample to a first temperature, the first temperature being within the physiological temperature range of the biological sample;

(b) performing an optical measurement on the biological sample at the first temperature;

(c) determining at least one optical parameter of a first layer of the biological sample, the first layer being located at a first depth of the biological sample, the first temperature corresponding to the first depth of the biological sample;

(d) changing the temperature of the biological sample to at least a second temperature, the at least second temperature being within the physiological temperature range of the biological sample;

(e) performing an optical measurement on the biological sample at the at least second temperature;

(f) determining the at least one optical parameter at at least a second layer of the biological sample, the at least second layer being located at at least a second depth of the biological sample, the at least second temperature corresponding to the second depth of the biological sample; and (g) determining the at least one parameter of the biological sample from the functional dependence of the at least one optical parameter on depth in the biological sample.

Disease states that can be diagnosed using the method of this invention include, diabetic state, peripheral vascular disease, a dermal disease state, or a neoplasmic disease state.

The method of this invention is applicable for use on the surface of any tissue wherein light can be introduced into a tissue boundary and re-emitted light intensity can be measured across the same or another tissue boundary, while temperature is being changed to affect a change in light penetration depth in tissue. Accordingly, a temperature-controlled endoscopic probe can be used to diagnose lesions ulcers on the surface of the esophagus or the surface of the cervix.

The method of this invention is applicable over a temperature range of from about 0° C. to about 45° C. A preferred temperature range is from about 10° C. to about 42° C., and a more preferred temperature range is from about 20° C. to about 40° C. Generally, the temperature range should be sufficient to provide a detectable change in light penetration depth in tissue without any temperature related injury to the tissue or any significant discomfort.

The method of this invention is applicable over a wavelength range of light of from about 400 nm to about 2500 nm. However, a wavelength range of light of from about 600 nm to about 1300 nm is preferable for diagnosing blood circulation related diseases, and a wavelength range of light of from about 1300 nm to about 2500 nm is preferred for analytes having long wavelength absorption bands.

The method of this invention can also be used to screen for disease state in a population by using the dependence of the light penetration depth on temperature and the effect of temperature on measured optical properties of tissue, based on expected statistical behavior of a normal population and deviation from such normal statistical behavior.

In another aspect, this invention provides an apparatus for determining the optical parameters of a biological sample. The apparatus comprises:

(a) a means for irradiating a region of the biological sample with light;

(b) a means for collecting light re-emitted from the biological sample;

(c) a means for changing the temperature of the biological sample to a temperature within the physiological range of the biological sample so that radiation penetrates to a specified depth in the biological sample, (d) a means measuring the intensity of the collected re-emitted light at a plurality of temperatures, wherein the measured intensities correspond to light re-emitted from different depths of the biological sample; and (e) a means for calculating at least one parameter of the biological sample from the dependence of at least one optical parameter on depth in the biological sample.

In the methods described herein, temperature can be changed by one or more of the following techniques:

(a) Temperature stepping, which involves changing the temperature of a tissue sample between at least two different predefined temperatures. Non-invasive measurements are performed at each of the two or more different temperatures, and the signals measured at the different temperatures are used for the determination of a disease state or the concentration of an analyte in the biological sample, which may be indicative of a disease state.

(b) Temperature cycling, which involves changing the temperature of the tissue under observation from one value to a second value and returning it back to the original value. Optical measurements are performed at the three temperature settings.

(c) Temperature modulation, which involves cycling the temperature repeatedly (i.e., changing the temperature repeatedly) between at least two different predefined temperatures. Non-invasive measurements are performed at the different temperatures, and the signals measured at these temperatures are used for the determination of a disease state or the concentration of an analyte in the biological sample, which may be indicative of a disease state.

(d) Continuous temperature change, which involves applying heat to a body part and continuously measuring the optical signals as the temperature is increasing. Alternatively, the temperature can be lowered by bringing the body part in contact with a cooling element and performing a series of optical measurements as the body part is cooled below its normal temperature.

In all instances several optical properties (e.g., absorption, scattering, transmission, reflectance) are measured at a plurality of temperatures and a set of optical parameters is calculated for each temperature. The values of these measured optical properties or calculated parameters ($\mu_s'$, $\mu_a$, anisotropy factor g, $\mu_{eff}$, $\delta$, transport optical mean free path $1/[\mu_s'+\mu_a]$, etc.) at different temperatures can be correlated with a parameter of a biological sample, such as, for example, the concentration of an analyte or a disease state index to generate a calibration relationship. This calibration relationship can be used for subsequent determination of the parameter of the biological sample.

In order to fully appreciate the effects of temperature variations on NI measurements, it may be helpful to review the theoretical description of light propagation in tissues. A discussion of optical properties of tissue and the effect of these properties on light scattering and absorption is provided below. The dependence of NI measurements on temperature of the tissue is also illustrated, and preferred embodiments for controlling the temperature of NI measurements are described.

Light fluence within a turbid sample such as human tissue sample, where light may under scattering events, is described in the art by the following formula:

$$I = I_o \exp(-\mu_{eff} z) \quad (1)$$

where I, $I_o$, and z are defined as above and $\mu_{eff}$ is defined as:

$$\mu_{eff} = \sqrt{(3\mu_a[\mu_a + \mu_s(1-g)])} = \sqrt{3\mu_a(\mu_a + \mu_s')} \quad (2)$$

Penetration of light into the tissue is expressed by the light penetration depth, $\delta$ which refers to the rate of light intensity decay in turbid media along the direction of light introduction. The light penetration depth is the reciprocal of the effective attenuation coefficient $\mu_{eff}$, wherein:

$$\delta = 1/\mu_{eff} = 1/\sqrt{3\mu_a(\mu_a + \mu_s')} \quad (3)$$

Light penetration depth is a statistical representation of the distance measured from the sample surface to the interior of the sample, and along the direction of the incident light, at which light intensity is attenuated to 1/e of its incident value, where e is the base of the natural logarithm. Light penetration depth corresponds to the depth in tissue wherein 37% of the incident light is maintained.

$$I(\text{at } d=\delta) = I_o/e = 0.371 \quad (4)$$

Because the value of $\delta$ depends on both $\mu_a$ and $\mu_s'$, an increase in either of $\mu_a$ or $\mu_s'$ will lead to a decrease in the light penetration depth $\delta$. Conversely, a decrease in the value of these two coefficients will lead to an increase in the light penetration depth of light in the tissue.

When tissue samples are irradiated at visible and near-infrared wavelengths of light, where the dimension (size) of the scattering material (particles such as cells) is close to the magnitude of the wavelength of light, The reduced scattering coefficient, $\mu_s'$, can be expressed using Mie theory as follows:

$$\mu_s' = 3.28\pi a^2 \rho (2\pi a n_{ex}/\lambda)^{0.37}(m-1)^{2.09} \quad (5)$$

where $\rho$ represents volume density, i.e., the number of particles per unit volume;

"a" represents the radius of the scattering particle (e.g., cells, mitochondria, or collagen fibrils);

$n_{ex}$ represents the refractive index of the medium (interstitial fluid);

$m=(n_{in}/n_{ex})$, the ratio of the refractive index of the scattering particle $n_{in}$ to the refractive index of the medium $n_{ex}$; and $\lambda$ represents the wavelength of the light.

See Graaff et al., "Reduced light-scattering properties for mixtures of spherical particles: a simple approximation derived from Mie calculations", Applied Optics, Vol. 31, No. 10 (1992) 1370–1376.

For a given incident wavelength of light, $\mu_s'$ changes directly with either the cell size, "a", or the refractive index ratio "m", as shown in Equation (5). Because the refractive index of the scattering particles, $n_{in}$, remains relatively constant, $\mu_s'$ is influenced mostly by $n_{ex}$ and particle radius "a".

Methods of determining $\mu_{eff}$, $\mu_s'$ and $\mu_a$ are known in the art. One of these methods is the measurement of diffuse reflectance of the skin tissue. In a diffuse reflectance measurement, the measured reflectance is a function of the reduced scattering coefficient $\mu_s'$, the absorption coefficient $\mu_a$, the refractive index of the scattering medium, and the refractive index of the surrounding layer, which is usually air.

One of the methods of measuring the absorption and scattering coefficients of tissue is referred to as spatially resolved diffuse reflectance, wherein the intensity of re-emitted light is a function of the distance of the light introduction site from the light collection site on the detection surface. In this method, the intensity of the light re-emitted from a sample is measured at several distances on the surface from the site at which light is introduced into the sample. Under certain conditions, intensity of the re-emitted light is related to the separation of the light introduction site from the light collection site by the relationship:

$$R(r) = K_o[\exp(-\mu_{eff} r)]/r \text{ or} \quad (6)$$

$$\text{Log}[r \cdot R(r)] = \text{Log}(K_o) - \mu_{eff} r \quad (7)$$

where, R(r) represents the intensity of light reflected from a sample at a light collection site, which is separated from the light introduction site by a distance r, $K_o$ is a constant, $\mu_{eff}$ is the effective attenuation coefficient, and Log($K_o$) represents the natural logarithm of a number $K_o$. Equation (7) can be used for calculating the change in $\mu_{eff}$, and hence the light penetration depth $\delta$, as a function of tissue temperature. The use of spatially resolved diffuse reflectance has been used in the examples of this invention, but the invention is not limited to spatially resolved diffuse reflectance. Other methods can be used to determine $\mu_{eff}$, such as, for example, frequency domain measurements, and diffuse reflectance measurements.

The ability to accurately determine $\mu_s'$ and $\mu_a$ separately depends on the use of a diffusion theory approximation and requires a certain ratio of the scattering coefficient to the absorption coefficient ($\mu_s' \gg \mu_a$). This requirement limits the wavelength range of the measurement to wavelengths where this relationship holds. The diffusion theory approximation also requires a large separation (sampling distance) between the light introduction site and the light collection site, and hence large mass, such as skull, the biceps, or the calves (U.S. Pat. No. 5,492,118). Diffusion theory is also based on the assumption that human tissue is a homogeneous medium, which is contrary to what is known in medical art. The structure of the skin is known in the art. Several layers are histologically distinguishable, i.e., the epidermis (including the stratum corneum), the dermis, and subcutaneous tissues. Each layer ranges from tens to hundreds of micrometers in thickness. In a preferred embodiment of this invention, the distance between the light introduction site and the light collection site (or sites) is kept small (<3 mm) to confine observation of light interaction with tissue to approximately 1 mm$^3$. The small sampling distance allows temperature to be controlled and modulated over such a small volume. The use of a small sampling distance limits the use of the diffusion theory approximation to aid in calculating optical parameters of tissue. One way to avoid the limitations of the diffusion theory approximation involves the use of numerical methods, such as the Monte Carlo calculation, to determine the scattering and absorption coefficients, $\mu_s'$ and $\mu_a$. The accuracy of the values so determined depends on the inputs to the model.

We have discovered that temperature changes affect tissue optical properties in one or more of the following ways:

(1) Increasing temperature increases flow of blood to the cutaneous volume monitored during the measurement. This increase in blood flow in turn increases the value of absorption coefficients at wavelengths of hemoglobin and water absorption in the 500 nm to 1100 nm region of the electromagnetic spectrum.

(2) Increasing temperature affects temperature dependent change in the absorption coefficient of water in the 900 nm to 2500 nm region of the electromagnetic spectrum. The absorption properties of water are known to be very sensitive to temperature changes.

(3) Changes in temperature also causes changes in the scattering properties of tissue. The scattering coefficient of tissue depends on the refractive index of the medium (interstitial fluid), cell size, and volume density of cells in the tissue as given by Equation (5). Temperature affects the refractive index of the ISF. Because approximately 90% of human tissue is water, the refractive index of ISF may be approximated by the refractive index of water which varies with temperature according to the equation:

$$n=1.3341+2.5185\ 10^{-5}T-3.6127\ 10^{-6}T^2+2.3707\ 10^{-8}T^3 \quad (9)$$

where n is the refractive index at the sodium D line ($\lambda$=589.3 nm) and T is the temperature in degrees Celsius. The relationship in Equation (9) is obtained by fitting the published refractive index data of water as a function of temperature to a third order polynomial.

According to this embodiment of the invention, the change in temperature leads to change in penetration depth of light in the sample. When light is introduced into the surface of a biological sample, such as the skin of a body part, the light is diffusely reflected. This diffusely reflected light is collected at one or more light collection sites located on the surface of the biological sample at different distances from the light introduction site. The intensity of the collected light is measured by a detector. Light will penetrate to given depth into the biological sample. For a given light collection site at a specified distance from the light introduction site, the average light penetration depth in a biological sample varies with temperature, as illustrated in FIG. 1. Light penetrates deeper in the biological sample when the temperature of the sample is lowered. Light penetrates to a shallower depth in the biological sample when the temperature is raised. The method of measuring light propagation in tissue can be one of several prior art methods such as a diffuse reflectance measurements, spatially resolved diffuse reflectance method, or frequency domain measurements. Alternatively the signal can be detected at a fixed separation distance from an illumination point as described in co-pending U.S. application Ser. No. 09/366,084, filed Aug. 3, 1999, assigned to the assignee of this application, and incorporated herein by reference.

The effect of samples and media on light will now be discussed. The color of the human skin is affected mostly by the contents of hemoglobin, melanin, and bilirubin, which are the major components in the skin that exhibit significant absorption in the visible and near infrared regions of the electromagnetic spectrum. The reddish color of the skin depends to a great extent on the quantity of blood in the upper layer of dermis. The black, yellow, or white skin colors of people originating from different races reflect to a great extent the content of melanin, which is located mainly in the lower layers of the epidermis. Concentrations of colored compounds can be determined from changes in tissue absorption coefficient. In the case of patients with jaundice, an excess amount of conjugated bilirubin will appear in blood and bloodless tissue in the skin.

Another important optical property of the skin is its scattering coefficient. In general, the critical factors that affect the skin's scattering coefficient are the densities, sizes, and shapes of the cells, and the refractive indexes of intercellular fluids and intracellular fluid. The epidermis is relatively uniform (though having several layers), and so is the upper dermis, in horizontal directions parallel to the sampling surface. However, deeper and deeper into the dermis and subcutaneous tissues, the skin becomes less and less homogeneous as capillaries, veins, various corpuscles, adipose tissues, etc., appear. Then, the effects of refractive index, cell size and cell shape on the scattering coefficient of the tissue becomes less important, as the macroscopic structures of the muscles and tissues become more pronounced. In the layers closest to the surface (e.g., epidermis and upper dermis), the cell sizes and shapes and the refractive indexes of fluids have a significant effect on the scattering coefficient. Analytes that may cause changes in the cell sizes and shapes and the refractive indexes of fluids can be tracked by measuring the scattering coefficient of these layers. For example, any analyte exhibiting significant concentration changes in the intracellular or intercellular fluids can cause the refractive index to change in these fluids. Change in concentration of analytes in the extracellular fluid can also result in changes in the sizes and the shapes of the cells because of osmolality changes in and around the cells. Compounds that may significantly affect these changes in the skin are salts, proteins, fatty acids, and sugars (mainly glucose).

The present invention involves methods and apparatus for the measurement of optical properties of tissue taken across a skin boundary, while accounting for the effects of skin layers on the properties measured and temperature variations during the measurement. The present invention allows measuring optical properties of different layers in the tissue at different depths as the temperature is modulated. The measurement of optical properties of tissue across a skin boundary is adversely affected by the non-homogeneity of the different layers of the skin. The effect of varying or modulating the temperature of the multiple layers of skin tissue on their measured optical properties has not been disclosed prior to this invention.

U.S. Pat. Nos. 5,057,695; 5,551,422; 5,676,143; 5,492,118; 5,419,321; 5,632,273; 5,513,642; and 5,935,062 are silent as to the effect of different layers of skin on optical measurements or the effect of temperature on light penetration through these various layers of the skin. These patents disclose no methods or apparatus that address these issues. Other prior art methods use wide sampling distances and a diffusion theory approach to map deep tissue layers. These prior art methods operate on large body masses, such as the skull, thigh, or large arm muscles. The tissue volume sampled by the light beams is too large to enable effective temperature control or effective temperature modulation over this volume. Studies of blood circulation in skin show that cutaneous microcirculation occurs at depths of 1 to 2 mm below the skin's epidermal surface (I. M. Braverman, "The Cutaneous Microcirculation: Ultrastructure and Microanatomical Organization", Microcirculation (1997) Vol. 4, No. 3, 329–340). Thus, measurement of optical properties close to the surface of the skin can provide useful information on the effect of blood circulation on the concentration of metabolites in tissues that are close to the surface of the skin. Also, studies of blood circulation close to the surface of the skin by means of laser Doppler flowmetry (referred to as LDF herein) have shown that laser Doppler flowmetry is a good tool for diagnosing peripheral circulatory disease.

Temperature is an important physiological parameter for most living species. In "warm-blooded" animals, such as birds and mammals, a group of reflex responses operate to maintain body temperature within a narrow range in spite of wide fluctuations in environmental temperature. In humans, the normal value for the oral temperature is 37° C., however, this temperature varies by about ±1° C. from individual to individual on account of differences in metabolic rate, age, and hormonal influences. The normal human core temperature undergoes a regular circadian fluctuation of 0.5° C. to 0.7° C.

Various parts of the body are at different temperatures, and the magnitude of the temperature difference between the parts varies with the temperature of the environment. The rectal temperature is representative of the temperature at the core of the body and varies least with changes in environmental temperature. The extremities are generally cooler than the rest of the body and, within a particular body part, the temperature of the tissue is lowest at the skin surface.

Variations in the temperature of the tissue affect other physiological variables, such as the perfusion rate. A rise in the temperature of the tissue triggers a homeostatic reflex, which enhances local blood flow in order to increase transfer of heat away from the skin. Cooling the tissue to approximately 25° C. decreases the perfusion rate; however, at much lower temperatures, the skin again takes on a ruddy color. Other factors, such as activity, infections, some malignancies or mental stress, can also modulate the perfusion rate. A familiar example is the change in skin coloration, which can accompany exercise, alcohol intake, or even a change in position from sitting to standing.

Use of heated laser Doppler probes and warming the skin before a laser Doppler flowmetry (LDF) measurement is also generally practiced in the art. LDF methods described in the art deal exclusively with the AC portion of the signal and the effect of temperature on the movement of red blood cells. Scattering due to stationary tissue components and the effect of temperature on such a scattering parameter is not discussed in the art.

Pulse oximetry is another field where light interaction with tissue is used for diagnostic purposes. Pulse oximetry measurements deal mainly with light absorbance at two wavelengths over the course of several cardiac pulses. Tissue scattering is a static component that is ignored in this measurement. Increasing temperature above the body core temperature (37±1° C.) is used to enhance the pulse by dilating the veins to a level that makes arterial motion the only observable pulse. Thus, the prior art of pulse oximetry is silent as to the effect of temperature on static tissue scattering. The prior art of pulse oximetry is silent as to the effect of temperature on the total absorption in tissue at wavelengths other than that of hemoglobin absorption. The prior art of pulse oximetry is also silent as the effect of temperature on the combined absorption and scattering parameters of tissue as expressed by the penetration depth of light. Prior art in the field of pulse oximetry is further silent as to the effect of temperature on light propagation in tissue and the use of temperature for diagnostic applications other than the determination of oxygen saturation. This invention provides diagnostic applications based on the effect of temperature on tissue optical properties that are not suggested by prior art in the field of pulse oximetry.

Prior art non-invasive methods for the determination of glucose quantitation involve introduction of light at a light introduction site, penetration of light through the skin boundary of a body part, and emergence of a signal through the same or another boundary of the body part. The structure of the skin and its surface boundary (stratum corneum) vary from individual to individual and according to an individual's disease state. Light penetration depth in skin tissue and the dependence of light penetration depth on the temperature of the measurement site and the structure of the skin tissue is not discussed in the prior art. The prior art is silent as to the effect of a disease state on the interaction of light with tissue and changes in light penetration depth in tissue.

Diabetes and other disease states causes structural changes to the skin that can affect its optical properties, response of these optical properties to changes in concentration of glucose or other analytes, and response of these optical properties to cutaneous temperature changes. R. G. Sibbald et al., "Skin and Diabetes", Endocrinology and Metabolism Clinics of North America, Vol. 25, No. 2 (1996) 463472, summarize a set of dermatological and skin structural effects that are associated with diabetes. Among these effects is thick skin, which may relate pathophysiologically to accelerated collagen aging with elastic fiber fraying and increased cross-linkage, resulting from glycosylation of collagen fibers. Another effect of diabetes is "yellow skin" which also results from glycosylation of dermal collagen. Change in dermal collagen structure in diabetic patients has been also reported by V. M. Monnier et al., "Skin Collagen Glycation, Glycoxidation, and Crosslinking Are Lower in Subjects With Long-Term Intensive Versus Conventional Therapy of Type 1 Diabetes", Diabetes, Vol. 48 (1999) 870–880. Further, V. J. James et al., "Use of X-ray Diffraction in Study of Human Diabetic and Aging Collagen", Diabetes, Vol. 40 (1991) 391–394, show a structural change in collagen skin fiber as a result of diabetes. The net effect of these findings is that the there are structural differences, i.e., size, level of crosslinking, and distribution of collagen fibers in the skin of diabetic subjects as compared with the skin of non-diabetic subjects. These differences will lead to a difference in the scattering characteristics of the skin of diabetic subjects, because they affect the terms in Equation (5). Thus, the response of scattering coefficient to changes in glucose or other analyte concentrations, and response of the scattering coefficient to cutaneous temperature changes are expected to be different for diabetic subjects as compared to their values for non-diabetic subjects.

Scattering properties of tissue can vary with temperature as a result of one or more of the following effects:

(a) an increase in temperature can decrease the refractive index of the interstitial fluid and increase the scattering coefficient of tissue;

(b) a change in refractive index of cell membranes as temperature is increased. In either case the refractive index mismatch "m" in Equation (5) increases as temperature is increased can increase scattering coefficient;

(c) cell size increases as temperature is increased, and hence the scattering coefficient increases.

The value of $\mu_s'$ increases as temperature of the forearm of human subjects increases between 20° C. and 40° C. A linear relationship is found between temperature and $\mu_s'$, with the slope of a plot of $\mu_s'$ vs. temperature ranging from 0.047 to 0.066 $cm^{-1 \circ} C.^{-1}$. The mean value of the slope was found to be 0.053±0.008 $cm^{-1 \circ} C.^{-1}$ for light at a wavelength of 590 nm. A similar phenomenon is expected to occur at longer wavelengths, except that the scattering coefficient will be smaller and changes in the water absorption bands will be much larger.

Increasing the temperature of the skin can also change the structural properties of the stratum corneum and the epidermis. Increasing the temperature of the skin can also change the fluid content of sweat glands. Both should affect the scattering properties of skin. The first effect could be reversible, but the latter may not be reversible. The change in the scattering coefficient has been found to be linear and reversible with temperature changes.

According to Equation (4), the light penetration depth, i.e., the distance in the direction perpendicular to the surface of the tissue that the intensity of light propagating through the tissue is decreased to 1/e of its incident value, is dependent on the values of the absorption and the scattering coefficients Temperature changes affect the values of $\mu_s'$ and $\mu_a$, in a reversible manner, over the physiological range observed (20° C. to 40° C.). Light penetration depth in tissue is, therefore, dependent on the temperature of the tissue at the measurement site. Light penetration depth in tissue should decrease when either or both of $\mu_s'$ and $\mu_a$ increase, i.e., when temperature is increased. Conversely, light penetration depth in tissue should increase when either or both of $\mu_s'$ and $\mu_a$ decrease, i.e., when temperature is lowered. An increase in $\mu_a$ increases the probability that a photon diffusing in the tissue is absorbed and hence limits its propagation in tissue. Conversely, an decrease in $\mu_a$ decreases the probability that a photon diffusing in the tissue is absorbed and hence increases its propagation distance in tissue, whereby a photon can interact with more scattering centers and/or penetrate into a deeper layer. An increase in $\mu_s'$ increases the probability that a photon diffusing in the tissue is back-scattered, and hence limits its propagation in tissue. In like manner, a decrease in $\mu_s'$ decreases the probability that a photon diffusing in the tissue is back-scattered, and hence increases its propagation distance in tissue. The net effect is that photons propagate deeper in tissue along the incident light trajectory when the temperature of the tissue is decreased. This propagation distance can be expressed as the penetration depth $\delta(\delta=1/\mu_{eff})$ for light propagating perpendicular to the surface of the tissue. The propagation distance of light expressed as light penetration depth decreases when the temperature of the tissue is increased. The embodiments of this invention delineate diagnostic methods based on changes in light penetration depth in tissue as temperature of the tissue changes.

EXAMPLES

The following non-limiting examples further illustrate the present invention.

Example 1

FIG. 2 through FIG. 5 illustrate an apparatus suitable for the measurement of optical properties, and hence the concentration of different analytes at various depths in tissue. Co-pending U.S. application Ser. No. 09/098,049, filed Nov. 23, 1998, assigned to the assignee of this application, describes in detail many of the components used in the apparatus of this application. The apparatus is capable of introducing light into the skin of human subjects and measuring the light re-emitted therefrom.

Figure 2:
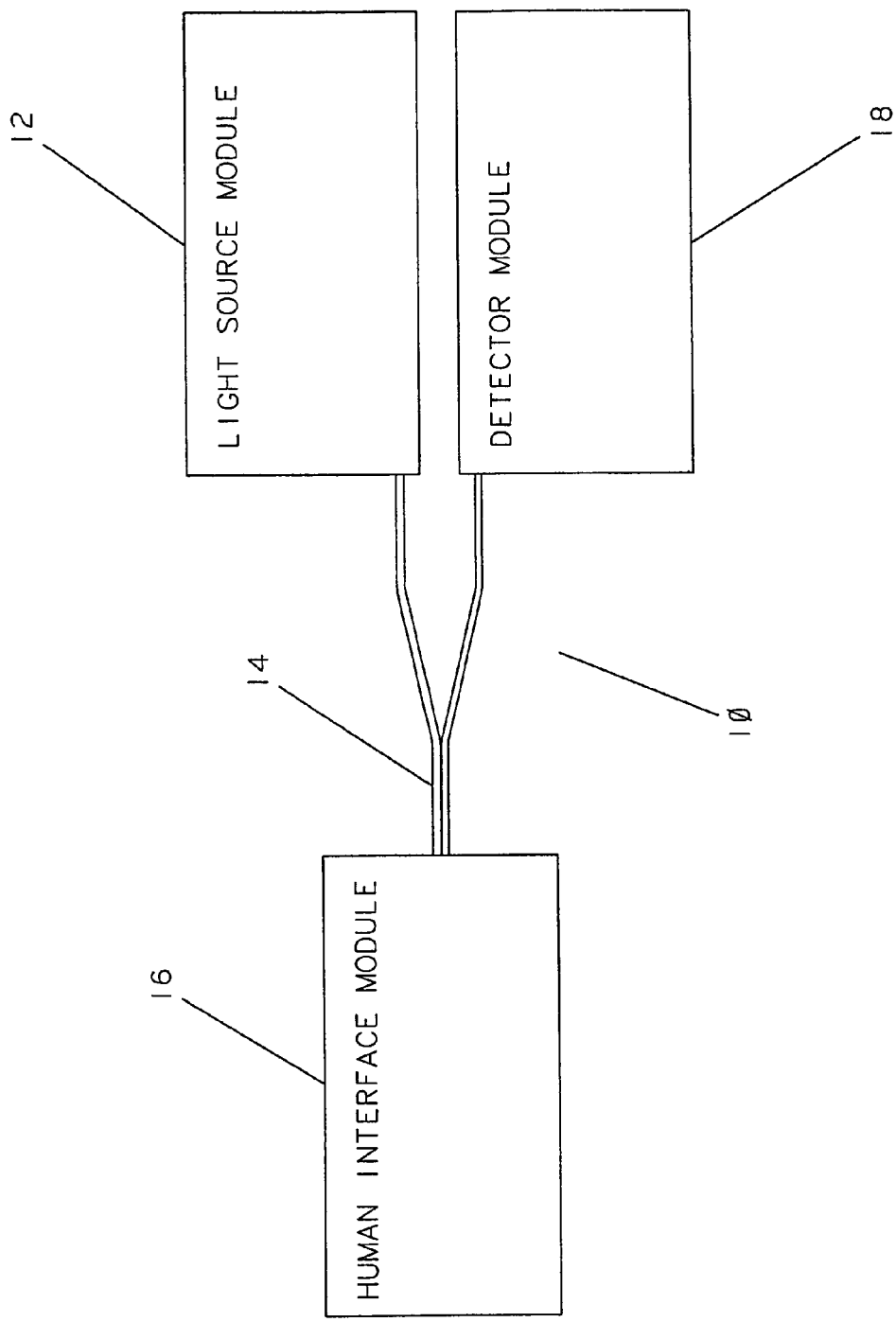
FIG. 2 is a block diagram illustrating an apparatus suitable for use in this invention.

FIG. 2 is a block diagram illustrating an embodiment of an apparatus 10 of this invention. The apparatus 10 comprises a light source module 12, a bifurcated optical fiber bundle 14, a human interface module 16, and a detector module 18. The light source module 12 includes a source of modulated light (not shown), such as a Gilway L1041 lamp modulated with a Stanford Research Optical Chopper. A prism, a dichroic beam splitter, or the like (not shown) may be used to direct a portion of the beam emerging from the light source module 12 to a reference detector (not shown), such as a Hamamatsu S-2386-44K 6C silicon detector, in order to normalize the measurements for fluctuations in intensity of the source of light. The rest of the light emerging from the light source module 12 is focused onto the end of a source tip 20 of a bifurcated fiber 14 by means of at least one focusing lens (not shown). See FIG. 3A. Additional optical elements (not shown), such as attenuators, optical filters, and irises may be inserted between the source of light and the source tip 20. The source tip 20 is preferably held in an adapter (not shown) having provisions for adjusting the location of the source tip with respect to the beam emerging from the source of light.

Figure 3A:
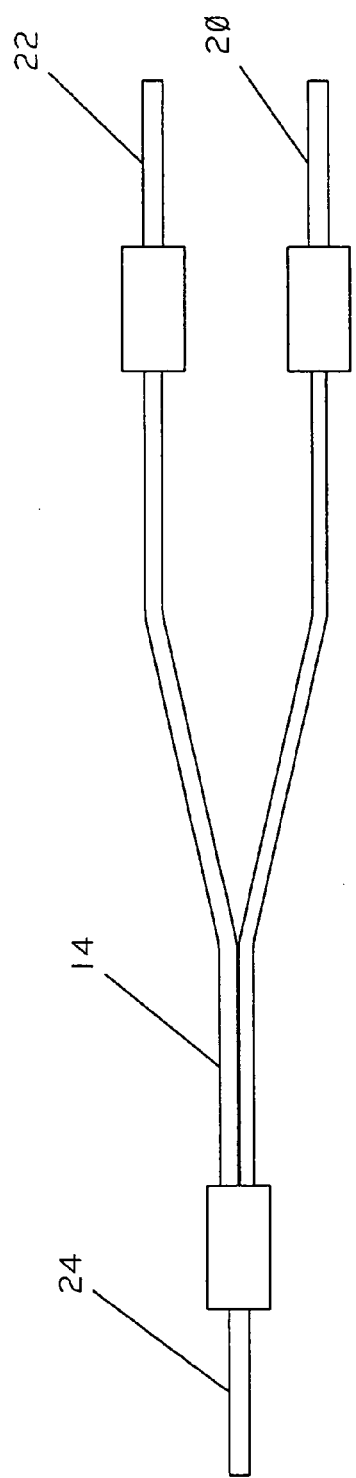
FIGS. 3A and 3B illustrate portions of a bifurcated optical probe.
Figure 3B:
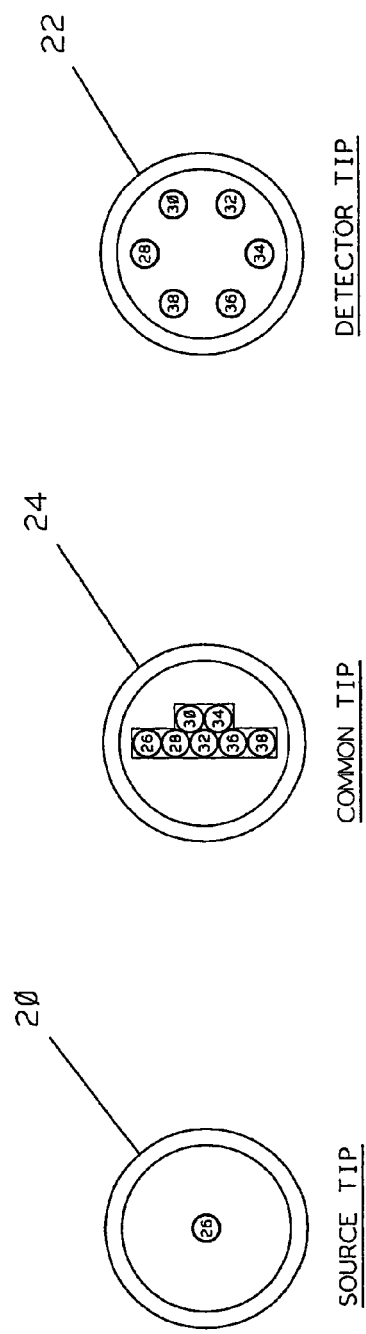

FIGS. 3A and 3B illustrate in detail a bifurcated optical fiber bundle 14.

The bifurcated optical fiber bundle 14 was constructed from Anhydrous G Low OH VIS-NIR optical fibers. Referring now to FIG. 3A, the bifurcated optical fiber bundle 14 comprises a source tip 20, a detector tip 22, and a common tip 24. The three distinct "tips" or termination sites of the bifurcated optical fiber bundle 14 are shown in FIG. 3B. During operation, the source tip 20 is contained within the light source module 12, the detector tip 22 is contained within the detector module 18, and the common tip 24 is contained within the human interface module 16. A single optical fiber 26 transmits light from the source tip 20 to the common tip 24. Six optical fibers 28, 30, 32, 34, 36, 38 transmit light from the common tip 24 to the detector tip 22.

The common tip 24 is installed in the human interface module 16, which is placed against a body part during use. As shown in FIG. 3B, the common tip 24 comprises the fiber 26 that transmits light from the source tip 20 to the common tip 24 and the six fibers 28, 30, 32, 34, 36, 38 that collect the light that is re-emitted from the tissue sample and transmit the collected light to the detector tip 22.

Figure 4:
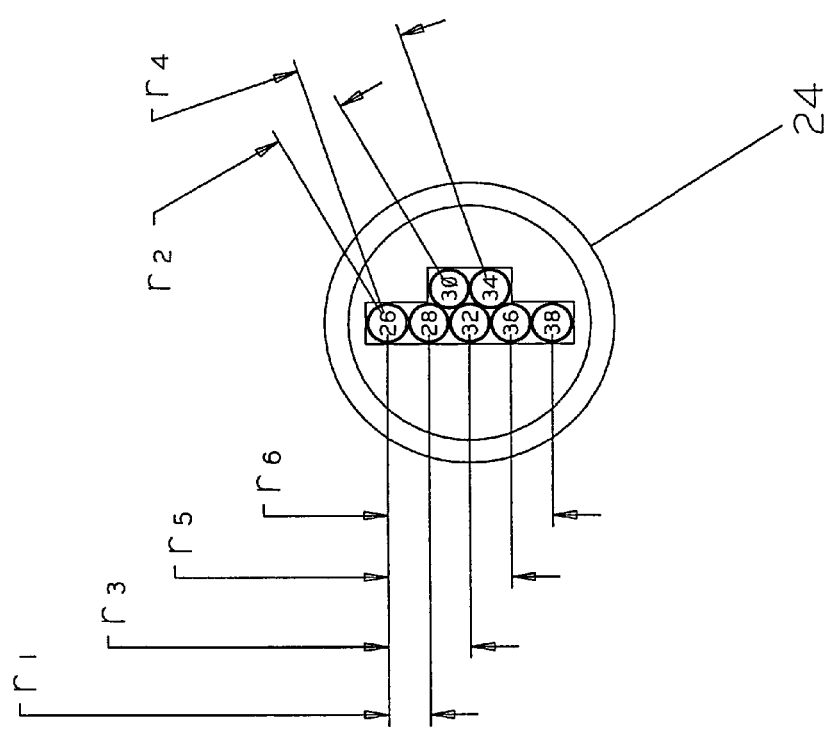
FIG. 4 illustrates the nominal separation distances, r, between light collecting elements and the illuminating element.

One end of each of the fibers 28, 30, 32, 34, 36, 38 is located within the common tip 24 at increasing distances from the fiber 26. The nominal separation distances, r, between the center of the fiber 26 and the centers of the fibers 28, 30, 32, 34, 36, 38 of the common tip 24 are shown in FIG. 4. All of the fibers 28, 30, 32, 34, 36, 38 are located at separation distances, r, that are less than 4 mm away, and, preferably, less than 2 mm away from the fiber 26.

The other ends of the fibers 28, 30, 32, 34, 36, 38 are arranged in a circle within the detector tip 22, as shown in FIG. 3B, with sufficient spacing to allow a shutter to interrogate each fiber individually. The detector module 18 receives the detector tip 22 and holds it adjacent to a rotating shutter (not shown) that allows detection of the light emitted from one fiber at a time. The shutter has a detent or other means to lock it in the six fiber positions. A pair of achromatic lenses (25 mm diameter, 60 mm focal length) focuses the light from the fiber of interest on a detector. The detector was a Hamamatsu S-2386-44K 6C silicon detector. The detector module 18 also comprises appropriate electronic signal processing instrumentation, such as large dynamic range amplifiers and lock-in amplifiers. Alternatively, the outputs of the six fibers can be directed to six detectors for parallel signal processing.

Figure 5:
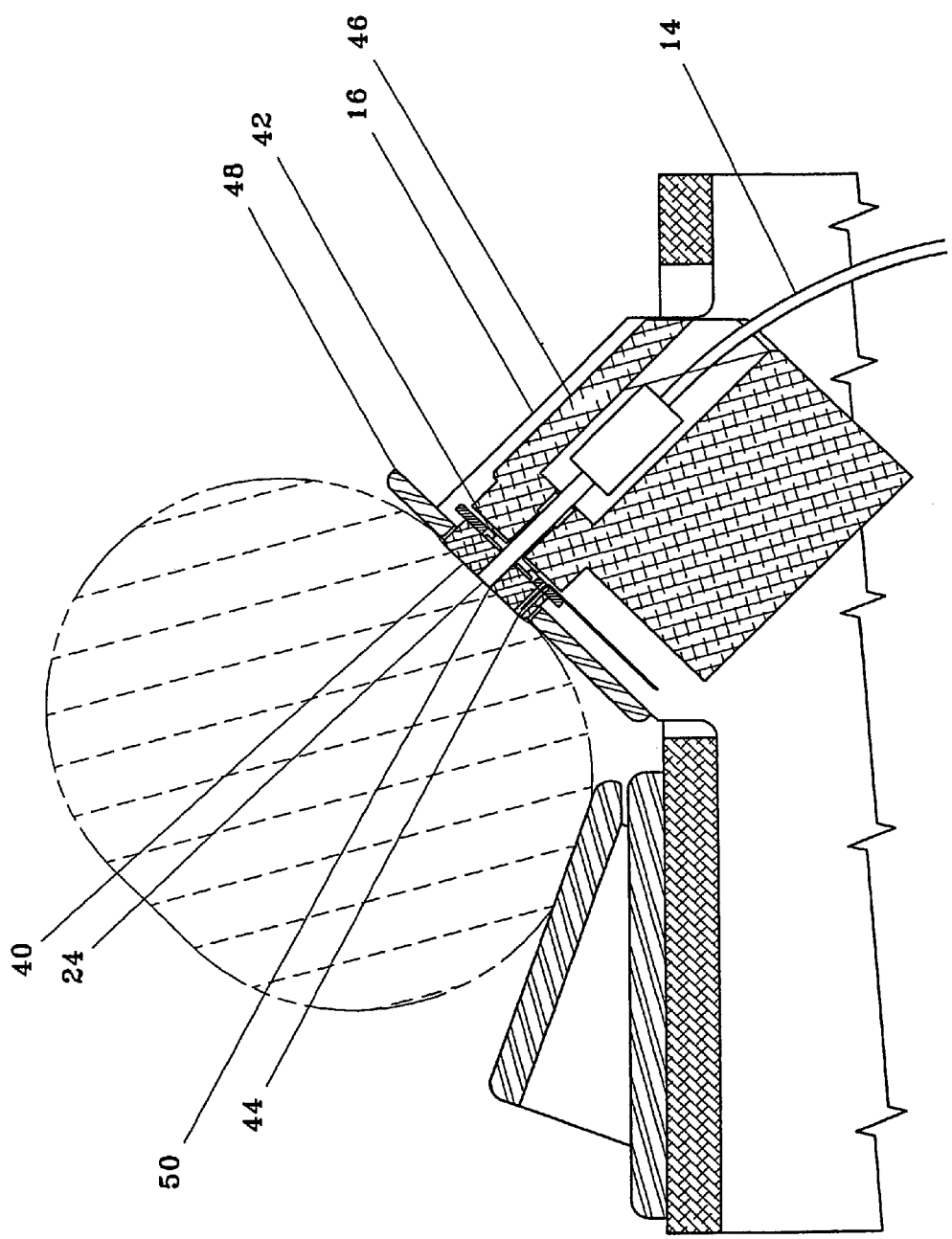
FIG. 5 illustrates a body interface for human volunteer experiments.

FIG. 5 illustrates the human interface module 16, which comprised an aluminum disk 40, a thermoelectric cooling element 42, a thermocouple 44, a heat sink 46, the common tip 24, and an interface adapter 48. The aluminum disk contained a through-hole that received the common tip of the fiber optic probe and holds the common tip 24 against the body part. The temperature of the aluminum disk 40 (and of the tissue adjacent the disk 40) was controlled by the thermoelectric element 42, such as a Marlow Industries model number SP1507-01AC. The Thermoelectric cooler/heater was powered by a temperature controller/power supply, such as a Marlow Industries model number SE5000-02. The heat sink 46 was provided on the back of the thermoelectric cooling element 42 to enhance heat transfer. The interface adapter 48 was shaped to conform to a body part and might, for example, be cylindrical, flat, spheroidal or any other shape that provided comfortable support to the body part. In addition, the human interface module may have a comfortable armrest (not shown) for the testing forearm.

The source fiber and the collection fibers were 400 μm in diameter. The distance from any one collection fiber to the source fiber 26 at the end of the common tip 24 defined the distance between the corresponding light collection site on the skin and the light introduction site, also on the skin. These distances were the sampling distances. These distances are indicated in FIG. 4 and listed in TABLE 1.

TABLE 1

|  | $r_1$ | $r_2$ | $r_3$ | $r_4$ | $r_5$ | $r_6$ |
|---|---|---|---|---|---|---|
| Sampling Distance (mm) | 0.44 | 0.78 | 0.92 | 1.22 | 1.40 | 1.84 |

The six collection fibers received the re-emitted light from the skin at the common tip 24 and transmitted the light to the detector tip 22 housed in the detector module 18. The ends of all of these fibers at the detector tip 22 were in the focal plane of a lens (not shown) for the detector (not shown). However, only when the shutter between the end of a particular fiber and the detector (not shown) was opened was the light signal from that fiber detected. Selection of a particular light collection fiber was achieved by the use of a programmable shutter that selected one of the six light collection fibers. The shutter was rotated a programmed number of steps or to a pre-selected detent on its mount. Filter selection, distance selection, and temperature selection were controlled by a computer using LabView® Software.

The spatially resolved diffuse reflectance curves obtained by this apparatus were analyzed by means of Monte Carlo simulation and a calibration grid generated with a set of absorbing and scattering phantoms. The absorption and scattering coefficients were determined from this grid. Temperature was varied over the range 20° C. to 42° C. and the diffuse reflectance data were determined. The Marlow controller was programmed to preset temperatures. Temperature was allowed to equilibrate before a set of optical data was collected. Temperature was measured by a thermocouple embedded in the element 42, which is brought in contact with the forearm of the subject. Temperature was calibrated by means of a Cole Palmer digital thermometer, a thermistor, and a set of water baths maintained at 0° C., 26° C., and 50° C. This calibration arrangement was further validated with a standard platinum resistance thermometer. Reflectance values at $r_1$, $r_3$, and $r_6$ were measured at different temperatures and wavelengths. Values of $\mu_a$ and $\mu_s'$ for each individual were determined at each temperature. The light penetration depth was calculated from the values of $\mu_a$ and $\mu_s'$ calculated for the same individual.

Example 2

Figure 6A:
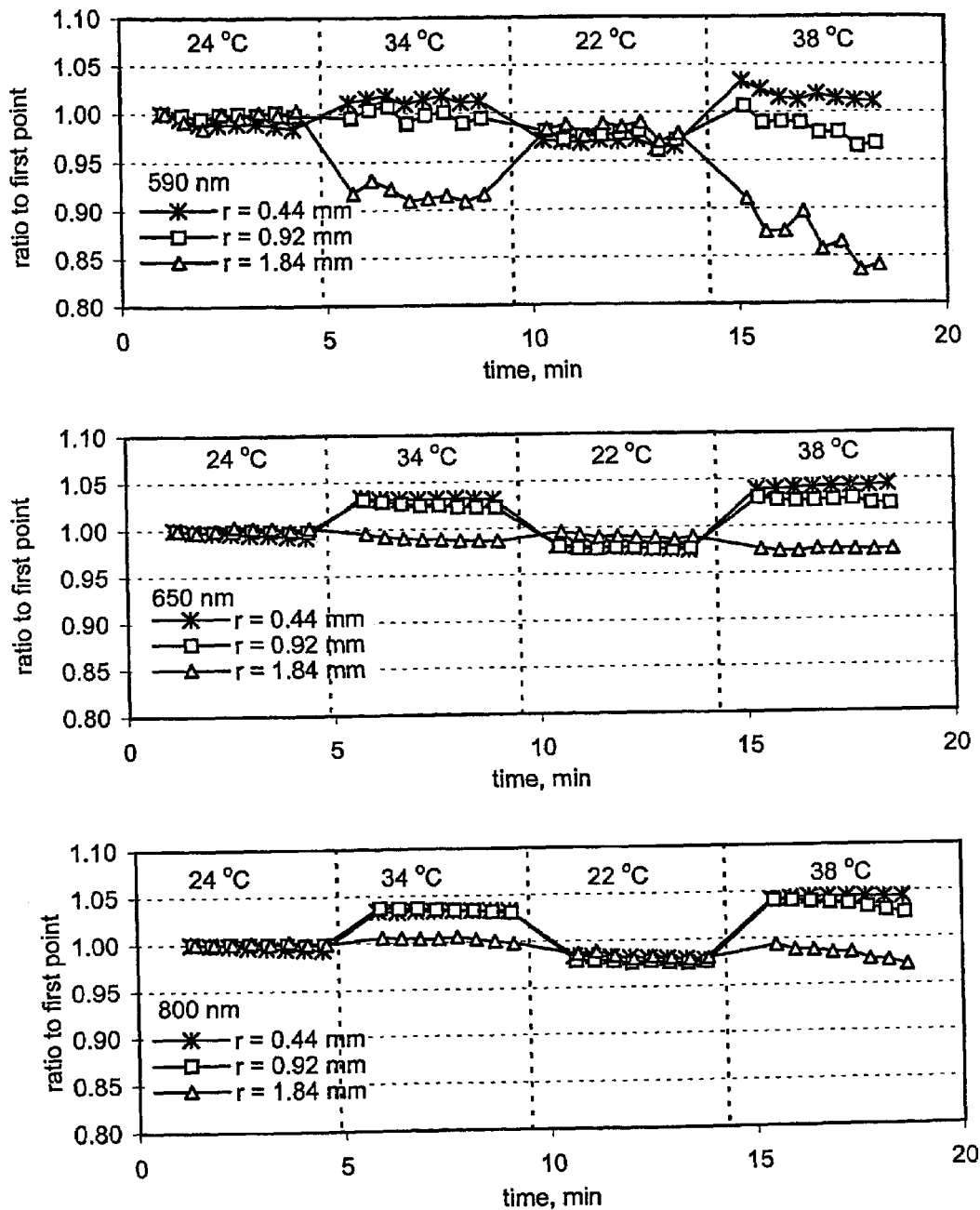
FIG. 6A shows the change in reflectance of human forearm skin as a function of temperature for light at wavelengths of 590 nm, 650 nm, and 800 nm.

The apparatus described in Example 1 was used to study the effect of temperature changes on the optical properties of human skin. FIG. 6A shows the change in reflectance as a function of temperature for a Caucasian subject for light having wavelengths of 590 nm, 650 nm, and 800 nm. The temperature was increased from 24° C. to 34° C., then lowered to 22° C. and finally raised to 38° C. The reflectance values are normalized to the value at 24° C. Temperature was maintained at each value for four (4) minutes during which the reflectance was measured; the transition between two temperatures consumed a period of about one minute. The $\mu_s'$ and $\mu_a$ values were determined by measuring spatially resolved diffuse reflectance in a temperature-controlled area of the human forearm.

Figure 6B:
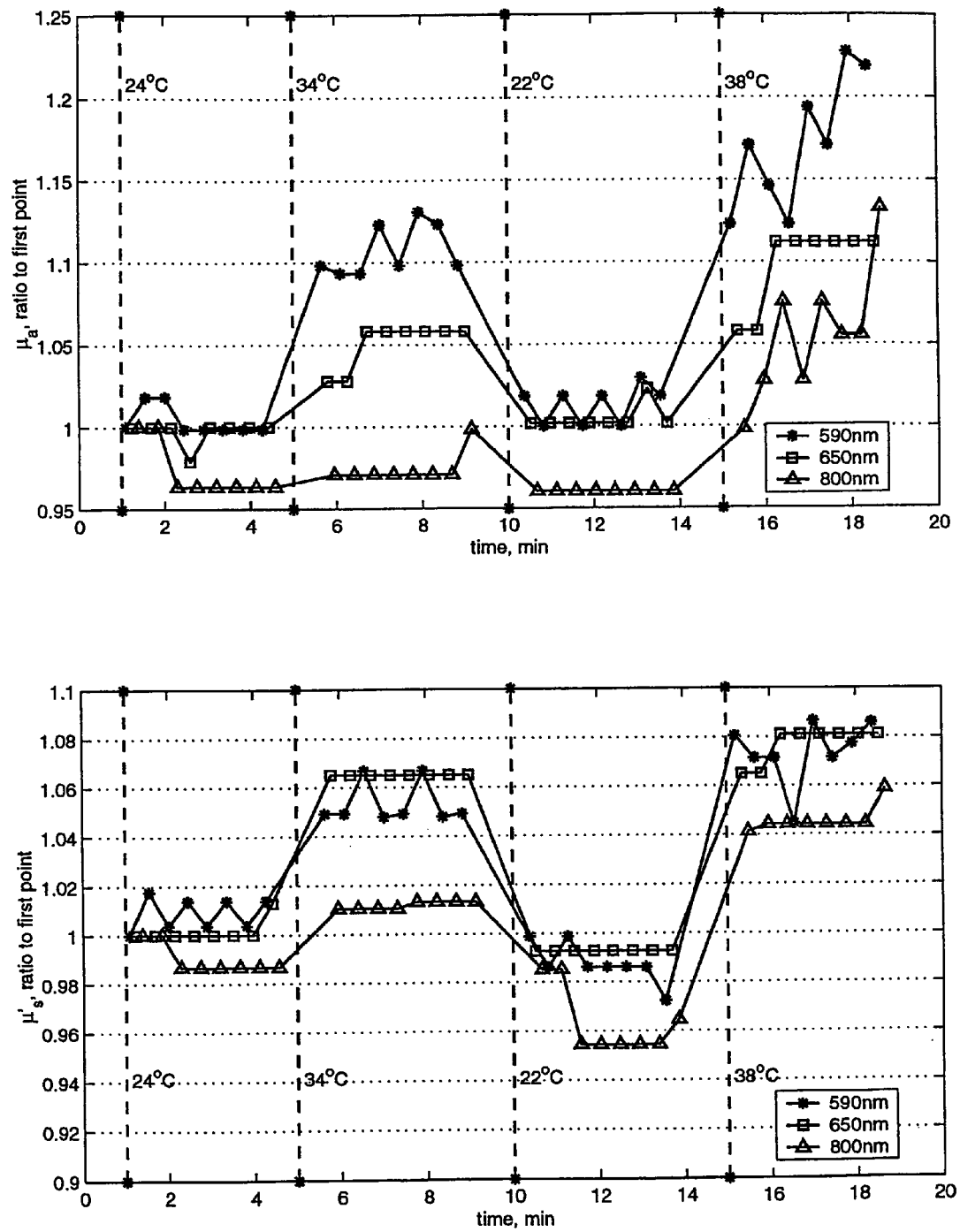
FIG. 6B shows the calculated values of $\mu_a$ and $\mu_s'$ for the same individuals for light at wavelengths of 590 nm, 650 nm, and 800 nm.

The normalized reflectance curves were analyzed by means of a Monte Carlo simulation and calibration grid generated with a set of absorbing and/or scattering phantoms to generate a calibration grid. The absorption and scattering coefficients were determined from this grid. FIG. 6B shows the calculated values of $\mu_a$ and $\mu_s'$ for the same individual. The step-wise behavior of $\mu_a$ and $\mu_s'$ followed the step-wise change in temperature at the measurement site.

Figure 7:
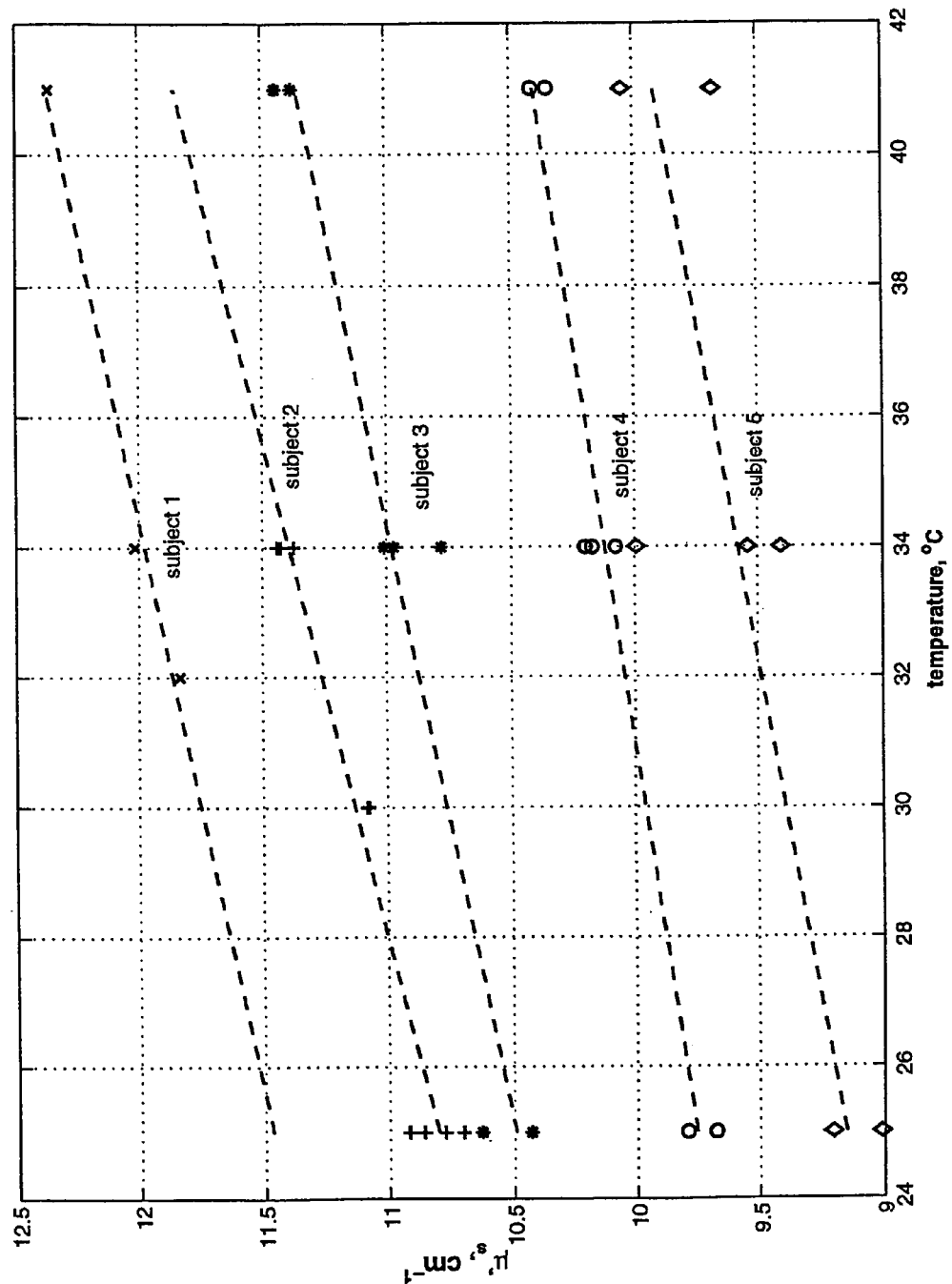
FIG. 7 is a plot of scattering coefficient as a function of temperature for different subjects.

FIG. 7 summarizes the relationship between temperature and $\mu_s'$ for measurements taken on the forearms of a number of human subjects with light having a wavelength of 590 nm. A linear relationship was observed, with the slopes of the plots of $\mu_s'$ vs. temperature ranging from 0.047 to 0.066 cm$^{-1\circ}$ C.$^{-1}$ for the subjects tested. The mean value of slope of the foregoing plots was 0.053±0.008 cm$^{-1\circ}$ C.$^{-1}$.

Example 3

The apparatus described in Example 1 was used to test the change in optical properties of the human forearm for several subjects of different skin color. Nine subjects were tested. Testing was performed at least two hours after the breakfast meal and was completed between 10 A.M. and 12 noon each day. Testing on nine individuals was performed over the period of several days. Two of the subjects were Type II diabetics. Temperature was varied between 38° C. and 22° C. Values of $\mu_s'$ and $\mu_a$ were calculated by means of the method described in Example 2 of this application.

The value of $\mu_{eff}$ was calculated using Equation (2). Light penetration depth $\delta$ for a given temperature was calculated as $\delta=1/\mu_{eff}$. Change in light penetration depth ($\Delta\delta$) as a result of changing temperature between 38° C. and 22° C. was then calculated. The following three tables summarize the changes in light penetration depth in tissue resulting from modulating temperature between 38° C. and 22° C. Data for light at a wavelength of 590 nm are given in TABLE 2, data for light at a wavelength of 750 nm are given in TABLE 3, and data for light at a wavelength of 950 nm are given in TABLE 4.

TABLE 2 shows the effect of temperature on light penetration depth in human forearm tissue for light at a wavelength of 590 nm.

TABLE 2

| | 22° C. | | | 38° C. | | | |
|---|---|---|---|---|---|---|---|
| Subject | $\mu_a$ (1/cm) | $\mu_s'$ (1/cm) | $\delta$ (mm) | $\mu_a$ (1/cm) | $\mu_s'$ (1/cm) | $\delta$ (mm) | $\Delta\delta$ (μm) |
| 1 | 2.209 | 8.204 | 1.20 | 2.825 | 8.763 | 1.01 | 195 |
| 2 | 2.495 | 9.059 | 1.08 | 3.253 | 10.176 | 0.87 | 202 |
| 3 | 2.143 | 8.768 | 1.19 | 2.698 | 9.045 | 1.03 | 168 |
| 4 | 2.335 | 9.022 | 1.12 | 2.736 | 9.620 | 0.99 | 128 |
| 5 | 2.061 | 9.673 | 1.17 | 2.493 | 9.945 | 1.04 | 137 |
| 6 | 2.524 | 11.060 | 0.99 | 3.184 | 11.444 | 0.85 | 140 |
| 7 | 2.442 | 8.849 | 1.10 | 2.819 | 9.223 | 0.99 | 109 |
| 8 | 1.404 | 9.812 | 1.45 | 1.974 | 11.015 | 1.14 | 315 |
| 9 | 2.892 | 8.760 | 0.99 | 3.327 | 9.252 | 0.89 | 102 |

As shown in TABLE 2, temperature affected light penetration depth in human forearm tissue for light at a wavelength of 590 nm. Light penetration depth in tissue was shallower for light at a wavelength of 590 nm due to the high absorbance of hemoglobin at this wavelength ($\mu_a=2.2$ cm$^{-1}$). In all subjects the penetration depth of light in tissue was greater at 22° C. Light penetration depth increased, on the average, by 178 μm as the temperature of the tissue was lowered from 38° C. to 22° C. It should be noted that subjects 2 and 8 had been previously diagnosed as Type II diabetics for several years. While the increase in light penetration depth upon cooling ranged from 102 to 195 μm for light at a wavelength of 590 nm for subjects 1 and 3–7, the increase in light penetration depth for the two long-term diabetic subjects 2 and 8 ranged from 202 and 315 μm for light at the same wavelength.

TABLE 3 shows the effect of temperature on light penetration depth in human forearm tissue for light at a wavelength of 750 nm.

TABLE 3

| | 22° C. | | | 38° C. | | | |
|---|---|---|---|---|---|---|---|
| Subject | $\mu_a$ (1/cm) | $\mu_s'$ (1/cm) | Penetration Depth, $\delta$ (mm) | $\mu_a$ (1/cm) | $\mu_s'$ (1/cm) | Penetration Depth, $\delta$ (mm) | $\Delta\delta$ (μm) |
| 1 | 0.993 | 6.591 | 2.10 | 1.138 | 6.938 | 1.90 | 200 |
| 2 | 0.674 | 7.018 | 2.54 | 1.158 | 8.185 | 1.75 | 781 |
| 3 | 0.802 | 6.893 | 2.32 | 1.115 | 7.105 | 1.91 | 417 |
| 4 | 0.919 | 7.106 | 2.13 | 1.027 | 7.400 | 1.96 | 163 |
| 5 | 0.897 | 7.405 | 2.12 | 1.126 | 7.800 | 1.82 | 293 |
| 6 | 1.028 | 9.307 | 1.77 | 1.312 | 9.766 | 1.51 | 257 |
| 7 | 0.976 | 7.000 | 2.07 | 1.088 | 7.266 | 1.92 | 154 |
| 8 | 0.391 | 7.136 | 3.36 | 0.665 | 7.800 | 2.53 | 930 |
| 9 | 1.150 | 7.081 | 1.88 | 1.295 | 7.267 | 1.58 | 143 |

As shown in TABLE 3, temperature affected light penetration depth in human forearm tissue for light at a wavelength of 750 nm. In all subjects, the penetration depth of light in tissue was greater at 22° C. than at 38° C. Light penetration depth increases, on the average, by 360 μm as the temperature of the tissue was lowered from 38° C. to 22° C. Similar to the observations for light at a wavelength of 590 nm, the increase in light penetration depth following cooling ranged from 143 to 417 μm for subjects 1 and 3–7 for light at a wavelength of 750 nm, while the increases in light penetration depth for the two long-term diabetic subjects 2 and 8 were 781 and 930 μm, respectively, for light at the same wavelength.

TABLE 4 shows the effect of temperature on light penetration depth in human forearm tissue for light at a wavelength of 950 nm.

TABLE 4

| | 22° C. | | | 38° C. | | | |
|---|---|---|---|---|---|---|---|
| Subject | $\mu_a$ (1/cm) | $\mu_s'$ (1/cm) | Penetration Depth, $\delta$ (mm) | $\mu_a$ (1/cm) | $\mu_s'$ (1/cm) | Penetration Depth, $\delta$ (mm) | $\Delta\delta$ (μm) |
| 1 | 0.952 | 5.391 | 2.35 | 1.139 | 5.707 | 2.07 | 282 |
| 2 | 0.711 | 5.737 | 2.70 | 1.208 | 6.707 | 1.87 | 830 |
| 3 | 0.938 | 5.736 | 2.31 | 1.109 | 5.755 | 2.09 | 215 |
| 4 | 0.912 | 5.930 | 2.31 | 1.006 | 6.095 | 2.16 | 150 |
| 5 | 0.964 | 6.034 | 2.22 | 1.141 | 6.187 | 2.00 | 225 |
| 6 | 1.128 | 7.925 | 1.81 | 1.386 | 8.286 | 1.58 | 230 |
| 7 | 0.952 | 5.851 | 2.27 | 1.039 | 5.967 | 2.14 | 128 |
| 8 | 0.356 | 5.351 | 4.05 | 0.738 | 6.153 | 2.56 | 1492 |
| 9 | 1.019 | 5.600 | 2.22 | 1.125 | 5.639 | 2.09 | 130 |

As shown in TABLE 4, temperature still affected light penetration depth in human forearm tissue for light at a wavelength of 950 nm. In all subjects, the penetration depth of light in tissue was greater at 22° C. that at 38° C. Light penetration depth increased, on the average, by 320 μm as the temperature of the tissue was lowered from 38° C. to 22° C. While the increase in light penetration depth upon cooling ranged from 126 to 282 μm for light at a wavelength of 950 nm for subjects 1 and 3–7, the increases in light penetration depth for the two long-term diabetic subjects 2 and 8 were 830 and 1492 μm, respectively, for light at the same wavelength.

At all three wavelengths, light penetration depth was inversely related to temperature. The effective attenuation coefficient $\mu_{eff}$ was directly related to temperature. As temperature increased, both the absorption and scattering coefficients increased, resulting in a decrease in light penetration depth. The value of the light penetration depth and change in light penetration depth as a function of temperature varied with the wavelength of the light propagating in the tissue. This phenomenon is due partly to the decrease in light absorption by the blood. Blood perfusion to the cutaneous layers decreases as the temperature of the skin is lowered. Because light penetration in tissue depends on both the values of the absorption and scattering coefficients, changing temperature causes change in these parameters, and hence, change in light penetration depth, up to several hundred micrometers.

Example 4

This example illustrates the use of the apparatus and method of this invention for the non-invasive tracking of glucose concentration changes during a meal tolerance test. The results show a good correlation between the optical properties of tissue, as measured by the method of this invention, and the concentration of glucose in blood, as measured by an invasive method. The same apparatus as described in Example 1 and a similar testing procedure as described in Example 2 were used for the in vivo determination of blood glucose level for three subjects. For each individual subject, a meal tolerance test protocol was used to induce changes in blood glucose level. Correlation between the measured reflectance values and blood glucose level determined in vitro was calculated, as was correlation between the derived absorption and scattering coefficients and blood glucose level determined in vitro.

Each subject fasted for at least eight (8) hours before the experiment. The reflectance signal, measured at the dorsal forearm of each subject, was determined at different points in time. Skin temperatures were controlled while the tests were conducted. The skin temperature was varied step-wise cyclically between 22° C. and 38° C. For each temperature step, the reflectance measurement was repeated four times, with each set of the four repetitions taken at three sampling distances (0.44 mm, 0.92 mm, and 1.84 mm) and at three wavelengths (590 nm, 800 nm and 950 nm). The data for each temperature step was taken over a period of about 100 seconds. Blood samples were obtained from each subject by means of a finger-stick every 5 to 15 minutes and the blood so obtained tested by means of a commercially available glucose meter. The measurement procedure was begun when the subject was in a fasting condition. After 10 to 20 minutes, the subject ingested a high sugar drink (commercially available fruit juice, 680 mL of liquid containing 100 to 120 grams sugar). The total duration of measurement consumed from about 90 minutes to about 120 minutes.

Figure 8A:
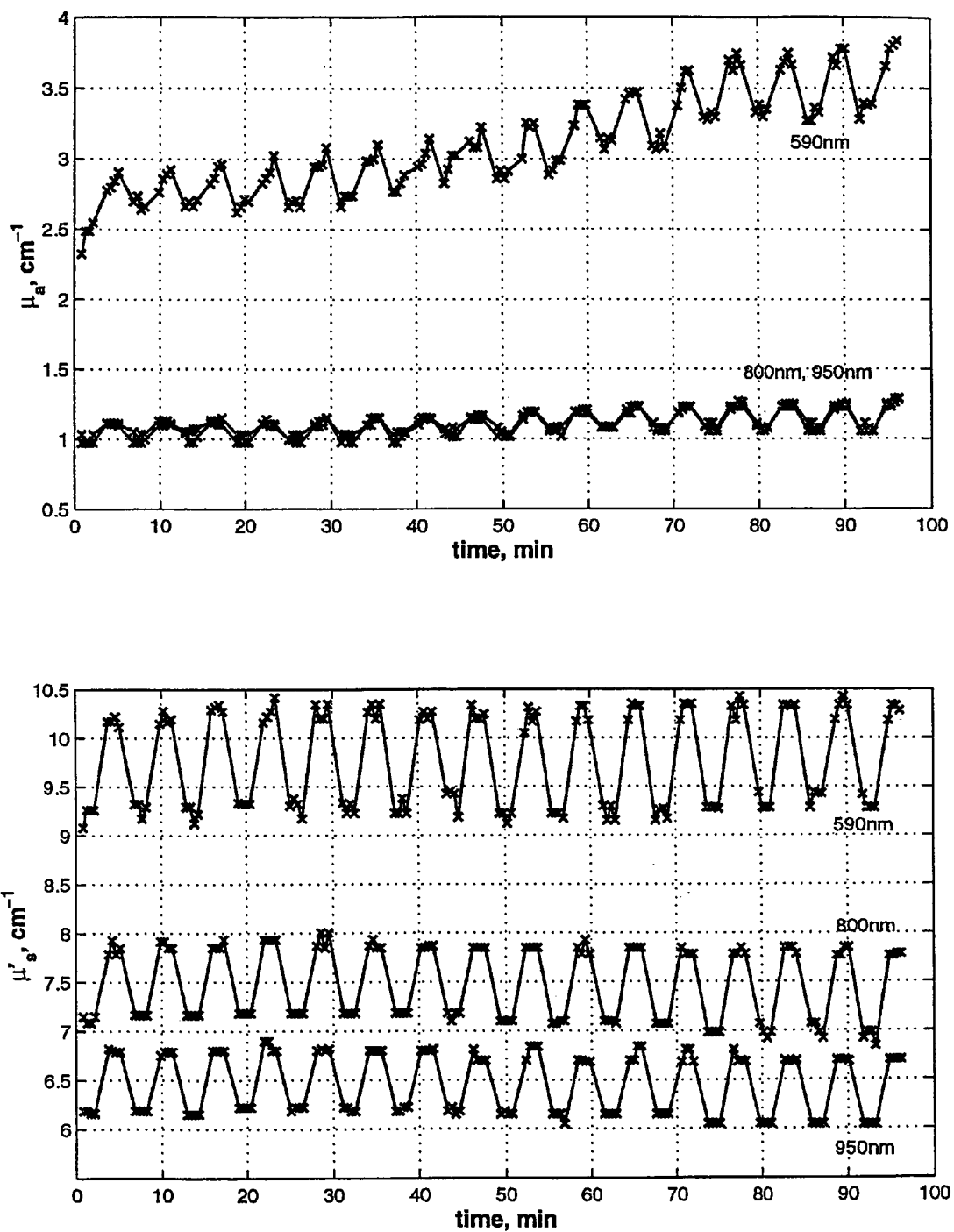
FIGS. 8A and 8B show the $\mu_s'$ and $\mu_a$ values for three subjects as temperature is varied cyclically between 22° C. and 38° C. during a meal tolerance test for light at wavelengths of 590 nm, 800 nm, and 950 nm.
Figure 8B:
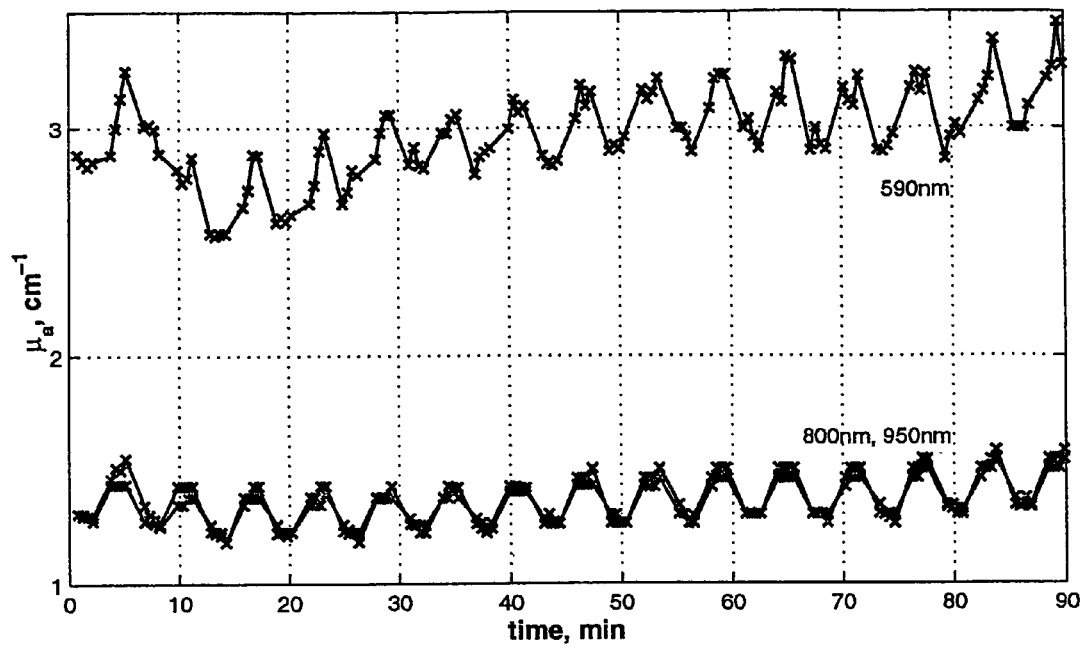
Figure 8B:
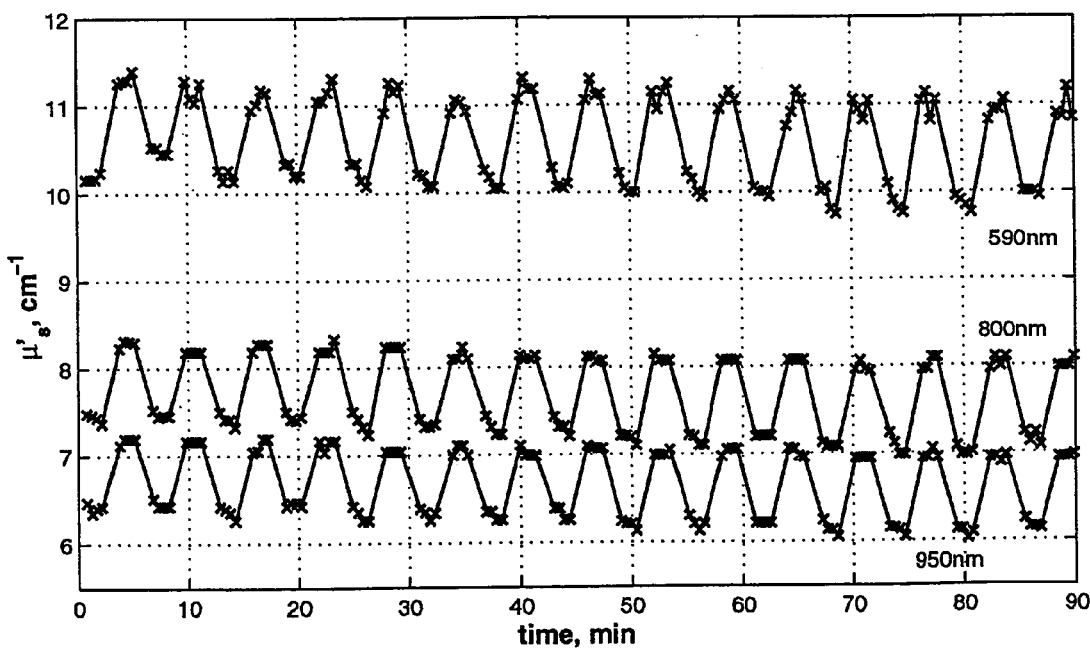

The values of $\mu_s'$ and $\mu_a$ were calculated from the reflectance data. FIGS. 8A and 8B show the $\mu_s'$ and $\mu_a$ values for two subjects as the temperature was cycled between 22° C. and 38° C. during a meal tolerance test. The regular reversible pattern in $\mu_s'$ and $\mu_a$ extended over the 90 minute duration of the experiment. The reproducible pattern in $\mu_s'$ indicated a reversible and instantaneous thermal effect on $\mu_s'$ over the duration of the experiment. This result suggested that no permanent change to tissue structure occurred as a result of temperature cycling between 22° C. and 38° C. Here, $\mu_a$ showed a similar pattern for light at wavelengths of 650 nm and 800 nm, while $\mu_a$ for light at a wavelength of 590 nm showed a gradual increase over time that was independent of temperature, in some instances.

Figure 9:
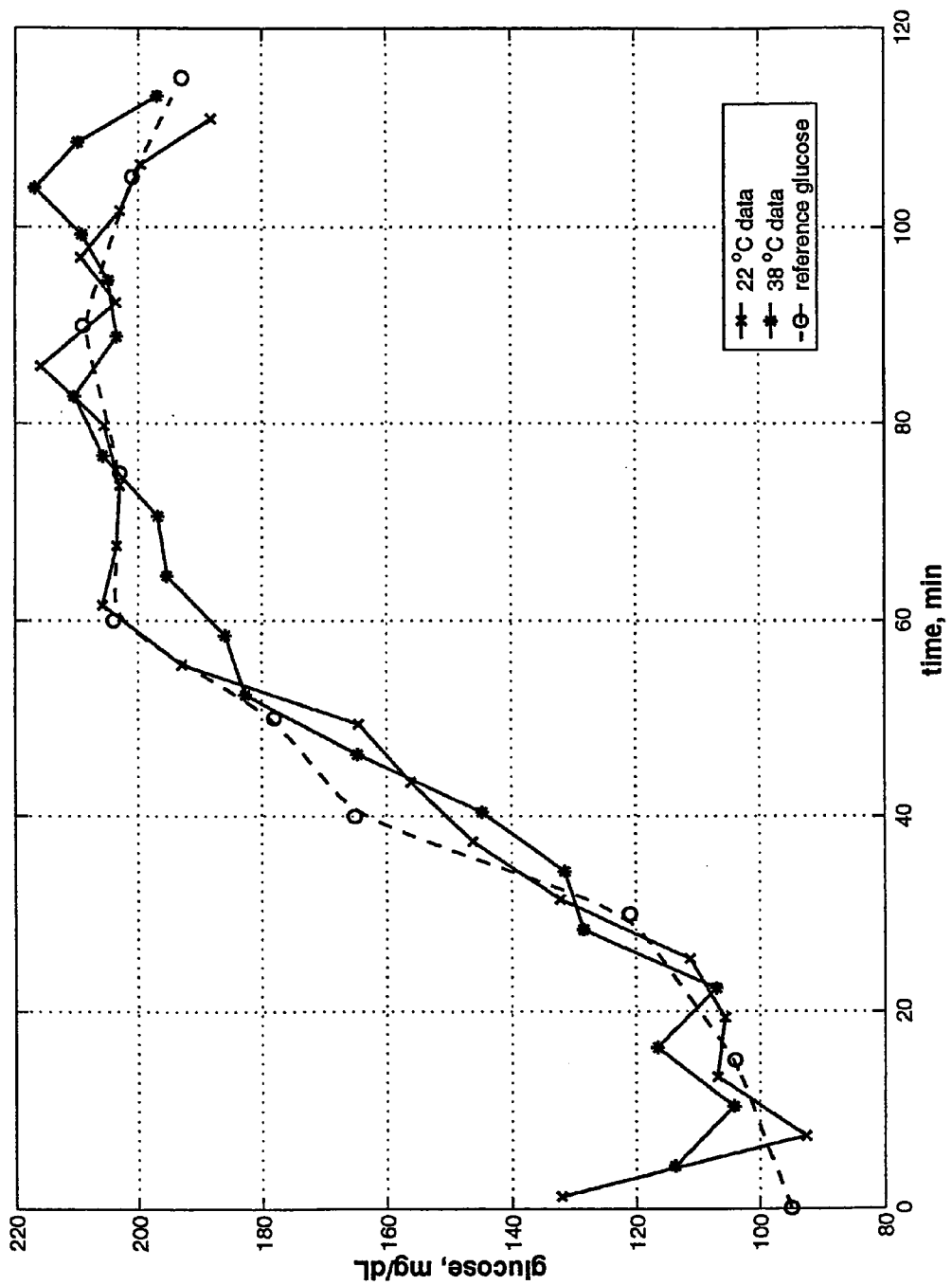
FIG. 9 shows the glucose calibration fitting for meal tolerance test data at 22° C. and 38° C., using a model based on absorption and scattering coefficients.
Figure 10:
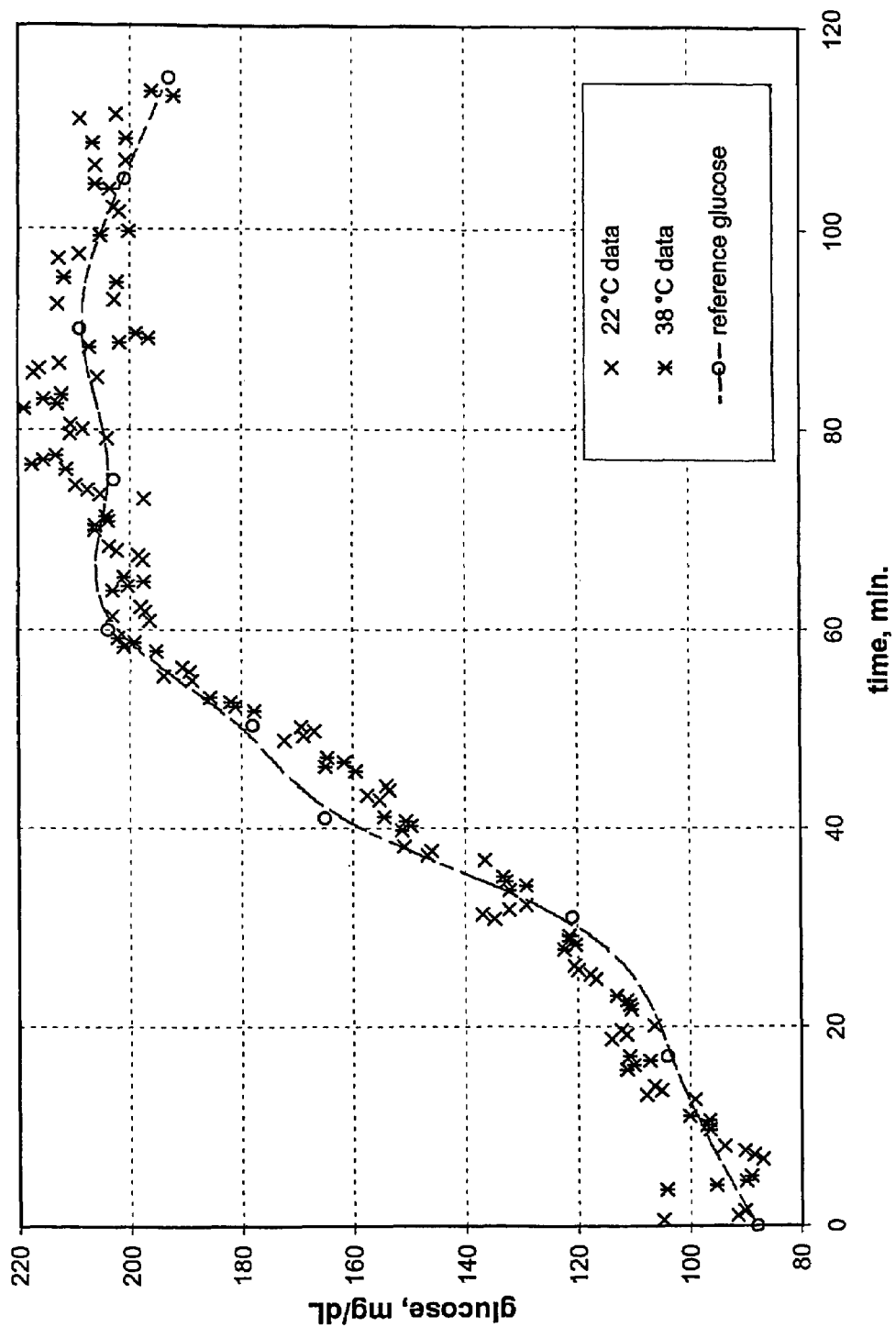
FIG. 10 shows the glucose calibration fitting for meal tolerance test data at 22° C. and 38° C., using a model based on reflectance values.

A plot of the blood glucose level as a function of time during the meal tolerance test for a third subject is shown in FIG. 9. The circles represent the points of the reference glucose test using capillary blood obtained by finger-stick and a home glucose meter (Glucometer Elite®, Bayer Corp., Elkhart, Ind.). The dashed line passing through these circles shows the fit values of reference glucose concentration resulting from cubic spline smoothing of the finger-stick capillary blood glucose level values. Interpolated data points represent the in vitro blood glucose test results at points in time that do not coincide with the points in time at which the tests were actually performed. The values of absorption and scattering coefficients were fitted to the blood glucose level values over the duration of the meal tolerance test using classical linear regression analysis. The values of the correlation coefficients at both 22° C. and 38° C. were 0.97, thereby indicating good calibration performance. Referring to FIG. 10, mathematical models based on reflectance data at three sampling distances and at three wavelengths fitted to the blood glucose level values over the duration of a meal tolerance test using classical linear regression analysis were obtained. These mathematical models resulted in correlation coefficients of 0.99 for meal tolerance tests at both 22° C. and 38° C., thereby indicating good calibration performance.

Alternatively, reflectance at a single distance was used as described in co-pending U.S. application Ser. No. 09/366,084, filed Aug. 3, 1999, assigned to the assignee of this application, and incorporated herein by reference. The correlation coefficient was found to be dependent on temperature and reached an optimal value at one particular distance at a given temperature. Classical linear regression was employed to correlate a model comprising reflectance measurement at each single sampling distance at three wavelengths with the interpolated values of reference glucose concentrations. TABLE 5 shows the correlation coefficients of the linear regression fitting at different temperatures and at different sampling distances during the meal tolerance test. At 38° C., the highest correlation coefficient obtained by linear least squares fitting of the data was at the sampling distance r=0.44 mm ($r_1$). At 22° C. the highest correlation coefficient obtained by linear least squares fitting of the data was at the sampling distance r=0.92 mm ($r_3$).

TABLE 5 shows the correlation between glucose values and skin reflectance at different temperatures.

TABLE 5

| | 22° C. | | | 38° C. | | |
|---|---|---|---|---|---|---|
| Subject | r = 0.44 mm | r = 0.92 mm | r = 1.84 mm | r = 0.44 mm | r = 0.92 mm | r = 1.84 mm |
| 1 | 0.806 | 0.808 | 0.766 | 0.807 | 0.786 | 0.727 |
| 2 | 0.783 | 0.886 | 0.8 | 0.867 | 0.899 | 0.873 |
| 3 | 0.851 | 0.931 | 0.879 | 0.932 | 0.927 | 0.92 |
| 4 | 0.964 | 0.981 | 0.96 | 0.984 | 0.946 | 0.915 |

Glucose concentration reference values and values of glucose calculated by using a model consisting of the combination of $\mu_a$ and $\mu_s'$ derived from all distances correlated well at both temperatures.

Example 5

This example illustrates the utility of the method of this invention for screening human subjects for incidence of diabetes. Twenty-nine (29) measurements were obtained from ten (10) subjects. Each subject was tested two to three times. Data were recorded between 10 A.M. and noon, generally two hours after a meal. Immediately before or after a diffuse reflectance measurement was performed on the dorsal side of the subject's forearm, the reference blood glucose level of the subject was measured by a glucose meter with blood obtained by finger-stick. Reflectance values were recorded for light at wavelengths of 590 nm, 800 nm, and 950 nm and at sampling distances of 0.4, 0.92, and 1.84 mm. The intensity of the light reflected at the three sampling distances was used to calculate $\mu_a$ and $\mu_s'$, and to derive values of the light penetration depth ($\delta$) at each wavelength. Measurements were taken nine times (at approximately four (4) minute intervals) with temperature at the measurement site set at 22° C.; then another nine measurements were taken as the temperature was raised to 38° C. and stabilized at that temperature.

Figure 11:
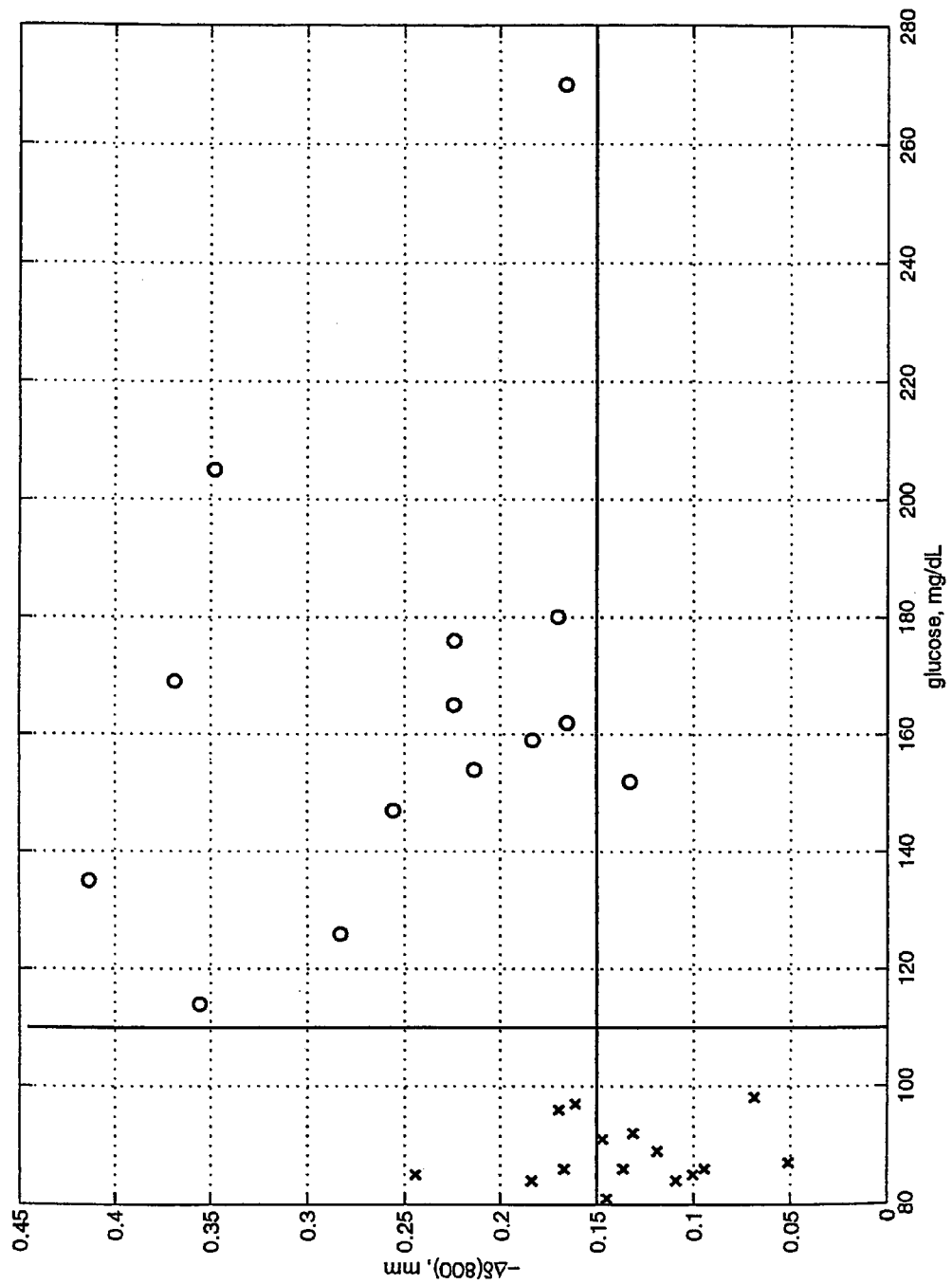
FIG. 11 illustrates the distribution of change in light penetration depth values as temperature is varied between 22° C. and 38° C. for different diabetic and non-diabetic subjects. The circles represent the data for diabetic subjects.

Reflectance data were assigned to either of two groups, based on the reference blood glucose level. Data associated with blood glucose levels below 110 mg/dl (15 data points) were assigned to Group 1. Data with blood glucose level above 110 mg/dl (14 data points) were assigned to Group 2. The data points of Group 2 were generated from three Type II diabetic subjects. The two groups showed significant differences in optical properties of the skin as the temperature was changed from 22° C. to 38° C. First, the subjects of Group 2 (diabetics) exhibited a larger increase in $\mu_a$ for light at wavelengths of 800 nm and 950 nm. Secondly, the decrease in light penetration depth in tissue ($-\Delta\delta$) for light at wavelengths of 800 nm and 950 nm was larger for the subjects of Group 2 (diabetics) than for the subjects of Group 1 (non-diabetics). Third, the average value of $\mu_a$ at 22° C. was lower for the subjects of Group 2 than for the subjects of Group 1. FIG. 11 shows a scatter plot of the data, wherein the decrease in light penetration depth $\delta$ in mm for light at a wavelength of 800 nm is shown on the y-axis is, and the glucose concentration determined invasively is shown on the x-axis. This plot shows that it is statistically possible to categorize a disease state, such as, for example, the diabetic state of a subject, using the method of this invention. For example, using a threshold level of 0.15 for the parameter $-\Delta\delta$, 23 out of the 29 data points of the studied subjects can be correctly categorized as either diabetic or non-diabetic.

TABLE 6

| Optical parameter | Group 1 | | | Group 2 | | |
|---|---|---|---|---|---|---|
| Wavelength, nm | 590 | 800 | 950 | 590 | 800 | 950 |
| Average $\Delta\delta$, mm | −0.14 | −0.14 | −0.17 | −0.14 | −0.25 | −0.32 |
| Average $\Delta\mu_a$, cm$^{-1}$ | 0.42 | 0.063 | 0.097 | 0.32 | 0.11 | 0.15 |
| Average $\Delta\mu_s'$, cm$^{-1}$ | 0.93 | 0.58 | 0.46 | 1.01 | 0.65 | 0.55 |
| Average $\delta$ at 22° C., mm | 1.09 | 2.03 | 2.12 | 1.18 | 2.34 | 2.46 |
| Average $\mu_a$ at 22° C., cm$^{-1}$ | 2.46 | 1.05 | 1.07 | 2.05 | 0.79 | 0.83 |
| Average $\mu_s'$ at 22° C., cm$^{-1}$ | 9.30 | 6.98 | 6.03 | 9.90 | 7.17 | 6.04 |

The data presented in FIG. 11 and in TABLE 6 show the feasibility of using the method and apparatus of this invention to test a population for possible incidence of diabetes. Such a test is painless and can be performed whenever there is a need for screening a large number of people to check for the risk of or the incidence of diabetes. Such a test can provide an early warning or point to cases of diabetes not previously diagnosed. Because the method is predicated upon measurement of change in the absorption and scattering parameters of tissue and blood components, correlation to other disease states that cause change in these parameters is possible. The method of this invention can be used for the purpose of diagnosing peripheral vascular disease, dermatological diseases, and neoplasmic diseases, where concentration of analytes in blood and circulation of blood differ from their state in normal tissues.

When the 64 optical data points obtained in this example and previous studies (Example 4) were fitted to the reference glucose values using a six (6) term generalized linear model, a linear fit with a correlation coefficient of 0.79 (standard error of calibration=28.8 mg/dl) resulted. The six terms of the model were: change of absorption ($\Delta\mu_a$ at 590 nm), $\Delta(1/\mu_a)$ at 590 nm and 950 nm, change of scattering ($\Delta\mu_s'$ at 590 nm), $\Delta(1/\mu_s')$ at 800 nm, and change in light penetration depth ($\Delta\delta$ at 950 nm).

Figure 12:
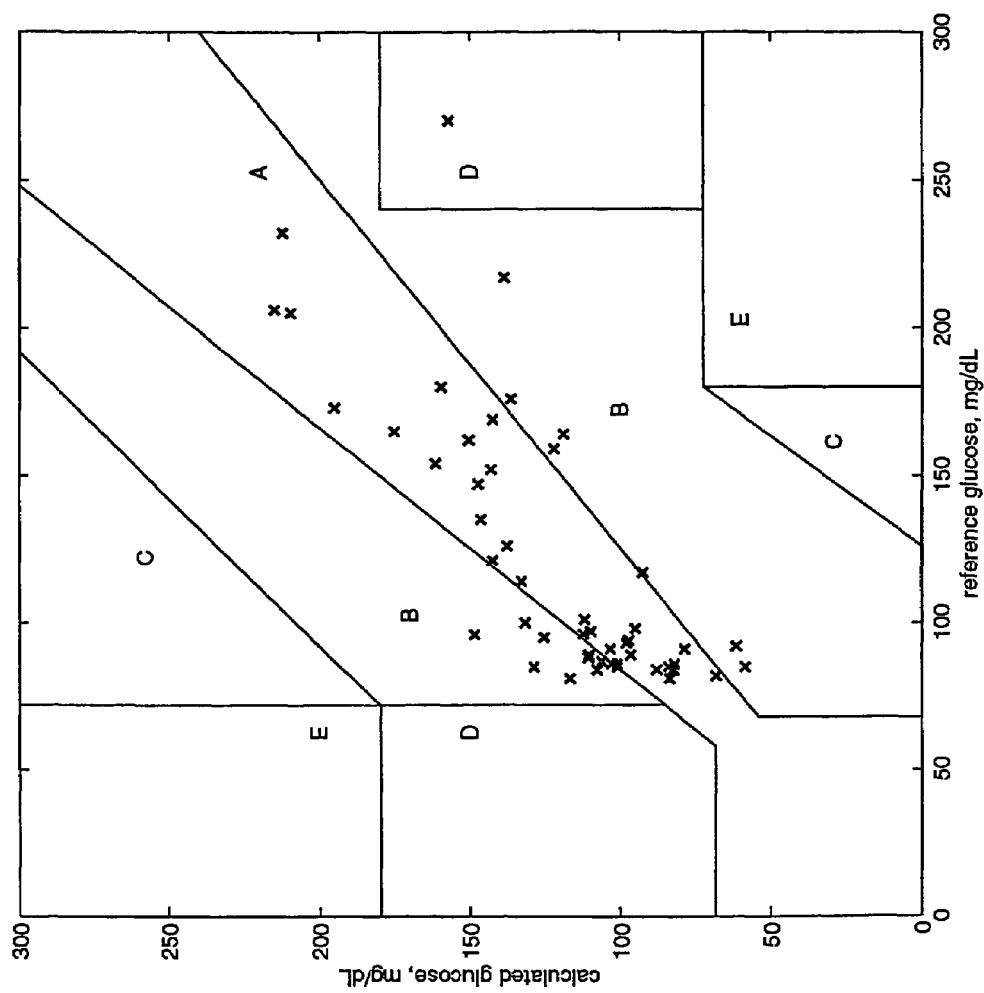
FIG. 12 illustrates calibration data for glucose values for several diabetic and non-diabetic subjects repeated several times and plotted as a Clarke error grid presentation.

FIG. 12 shows the results of the 6-term fitting to the glucose values. The 64 data points were plotted in the form of Clark error grid and show that a calibration relationship between blood glucose levels measured invasively and calculated blood glucose levels was established for the test subjects, with an acceptable scatter of data points. The majority of the data points were in the "A" zone of the Clark error grid. The Clark error grid presentation is a method of displaying performance data of glucose meters. Blood glucose levels determined by the test method are plotted against blood glucose levels determined by a reference method, i.e., an invasive method. Performance of the test method is deemed acceptable when the majority of the data points fall in the "A" and "B" zones, primarily in the "A" zone. Data points falling in the C, D, and E zones of the plot indicate that the test method is giving erroneous results that may lead to erroneous clinical intervention.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method of measuring at least one optical parameter of intact human tissue, wherein said at least one optical parameter is selected from the group consisting of absorption coefficient, scattering coefficient, mean free path, effective attenuation coefficient, and light penetration depth, said method comprising the steps of:
    (a) setting the temperature of said intact human tissue to a first temperature and allowing said intact human tissue to equilibrate at said first temperature before optical data are collected at said first temperature, said first temperature being within the range of from about 0° C. to about 45° C.;
    (b) performing an optical measurement on said intact human tissue at said first temperature, wherein said optical measurement is a spatially resolved diffuse reflectance measurement;
    (c) determining at least one optical parameter of said intact human tissue from said spatially resolved diffuse reflectance measurement at said first temperature, wherein said at least one optical parameter is selected from the group consisting of absorption coefficient, scattering coefficient, mean free path, effective attenuation coefficient, and light penetration depth, said first temperature corresponding to a first depth in said intact human tissue;
    (d) changing said first temperature of said intact human tissue to at least a second temperature and allowing said intact human tissue to equilibrate at at least said second temperature before optical data are collected at said at least said second temperature, said at least second temperature being within the range of from about 0° C. to about 45° C.;
    (e) performing said an optical measurement on said intact human tissue at said at least second temperature, wherein said optical measurement is a spatially resolved diffuse reflectance measurement;
    (f) determining said at least one optical parameter of said intact human tissue from said spatially resolved diffuse reflectance measurement at at least a second temperature, wherein said at least one optical parameter is selected from the group consisting of absorption coefficient, scattering coefficient, mean free path, effective attenuation coefficient, and light penetration depth, said at least second temperature corresponding to a second depth in said intact human tissue; and (g) determining said at least one parameter of said intact human tissue from the functional relationship of said at least one optical parameter on depth in said intact human tissue, wherein said optical measurements in step (b) and step (e) are carried out by transmitting light into a region of said intact human tissue at a light introduction site and collecting light re-emitted from said region of intact human tissue at a light collection site, wherein the distance between any light introduction site and any light collection site is less than three millimeters.

2. The method of claim 1, wherein said change in temperature of said intact human tissue results in a change in penetration depth of light in said intact human tissue.

3. The method of claim 1, wherein said first temperature and said at least second temperature are within a range from about 15° C. to about 45° C.

4. The method of claim 1, wherein said optical measurement is performed using light at at least one wavelength in a range from about 400 nm to about 2500 nm.

5. The method of claim 1, wherein said optical measurement is performed using light at at least one wavelength in a range from about 600 nm to about 1300 nm.

6. The method of claim 1, wherein said at least one parameter of said intact human tissue is the concentration of an analyte.

7. The method of claim 6, wherein said analyte is glucose, hemoglobin, or water.

8. The method of claim 1, wherein said intact human tissue is intact human skin, esophagus tissue, intestine tissue, or cervical tissue.

9. The method of claim 1, wherein said at least one parameter of said intact human tissue is a parameter indicating a disease state.

10. The method of claim 9, wherein said disease state is diabetic state, vascular disease state, dermatological disease state, or neoplasmic disease state.

11. A method of measuring at least one optical parameter of intact human tissue having a plurality of layers, wherein said at least one optical parameter is selected from the group consisting of absorption coefficient, scattering coefficient, mean free path, effective attenuation coefficient, and light penetration depth, said method comprising the steps of:

(a) setting the temperature of said intact human tissue to a first temperature and allowing said intact human tissue to equilibrate at said first temperature before optical data are collected at said first temperature, said first temperature being within the range of from about 0° C. to about 45° C.;

(b) performing an optical measurement on said intact human tissue at said first temperature, wherein said optical measurement is a spatially resolved diffuse reflectance measurement;

(c) determining at least one optical parameter of a first layer of said intact human tissue from said spatially resolved diffuse reflectance measurement, said first layer being located at a first depth of said intact human tissue, said first temperature corresponding to a first depth of said intact human tissue, wherein said at least one optical parameter is selected from the group consisting of absorption coefficient, scattering coefficient, mean free path, effective attenuation coefficient, and light penetration depth;

(d) changing said first temperature of said intact human tissue to at least a second temperature and allowing said intact human tissue to equilibrate at said at least second temperature before optical data are collected at said at least second temperature, said at least second temperature being within the range of from about 0° C. to about 45° C.;

(e) performing said an optical measurement on said intact human tissue at said at least second temperature;

(f) determining said at least one optical parameter at at least a second layer of said intact human tissue from said spatially resolved diffuse reflectance measurement, said at least second layer being located at at least a second depth of said intact human tissue, said at least second temperature corresponding to said second depth of said intact human tissue, wherein said at least one optical parameter is selected from the group consisting of absorption coefficient, scattering coefficient, mean free path, effective attenuation coefficient, and light-penetration depth; and (g) determining said at least one parameter of said intact human tissue from the functional dependence of said at least one optical parameter on depth in said intact human tissue, wherein said optical measurements in step (b) and step (e) are carried out by transmitting light into a region of said intact human tissue at a light introduction site and collecting light re-emitted from said region of intact human tissue at a light collection site, wherein the distance between any light introduction site and any light collection site is less than three millimeters.

12. The method of claim 11, wherein said change in temperature of said intact human tissue results in a change in penetration depth of light in said intact human tissue.

13. The method of claim 11, wherein said first temperature and said at least second temperature are within a range from about 10° C. to about 42° C.

14. The method of claim 11, wherein said optical measurement is performed using light at at least one wavelength in a range from about 400 nm to about 2500 nm.

15. The method of claim 11, wherein said optical measurement is performed using light at at least one wavelength in a range from about 600 nm to about 1300 nm.

16. The method of claim 11, wherein said at least one parameter of said intact human tissue is the concentration of an analyte.

17. The method of claim 16, wherein said analyte is glucose, hemoglobin, or water.

18. The method of claim 11, wherein said intact human tissue is intact human skin, esophagus tissue, intestine tissue, or cervical tissue.

19. The method of claim 11, wherein said at least one parameter of said intact human tissue is a parameter indicating a disease state.

20. The method of claim 19, wherein said disease state is diabetic state, vascular disease state, dermatological disease state, or neoplasmic disease state.

21. An apparatus for measuring at least one optical parameter of intact human tissue, wherein said at least one optical parameter is selected from the group consisting of absorption coefficient, scattering coefficient, mean free path, effective attenuation coefficient, and light penetration depth, said apparatus comprising:
  (a) a source of light for irradiating a region of said intact human tissue with light at at least one light introduction site;
  (b) a means for collecting light re-emitted from said region of said intact human tissue at at least one light collection site, wherein the distance between any light introduction site and any light collection site is less than three millimeters;
  (c) a means for changing the temperature of said intact human tissue to a temperature ranging from about 0° C. to about 45° C. so that radiation penetrates to a specified depth in said intact human tissue;
  (d) a detector for measuring the intensity of the collected re-emitted light at a plurality of temperatures, wherein the measured intensities correspond to light re-emitted from different depths of said intact human tissue, wherein said intensity of said collected re-emitted light is used to determine spatially resolved diffuse reflectance of said intact human tissue; and
  (e) a means for calculating at least one parameter of said intact human tissue from said spatially resolved diffuse reflectance and the dependence of at least one optical parameter on depth in said intact human tissue, wherein said at least one optical parameter is selected from the group consisting of absorption coefficient, scattering coefficient, mean free path, effective attenuation coefficient, and light penetration depth.

22. The apparatus of claim 21, wherein said change in temperature of said intact human tissue results in a change in penetration depth of light in said intact human tissue.

23. The apparatus of claim 21, wherein said light used to irradiate said intact human tissue has at least one wavelength ranging from about 400 nm to about 2500 nm.

24. The apparatus of claim 21, wherein said light used to irradiate said intact human tissue has at least one wavelength ranging from about 600 nm to about 1300 nm.

25. The apparatus of claim 21, wherein said at least one parameter of said intact human tissue is the concentration of an analyte.

26. The method of claim 25, wherein said analyte is selected from the group consisting of glucose, hemoglobin, and water.

27. The apparatus of claim 21, wherein said intact human tissue is selected from the group consisting of intact human skin, esophageal tissue, intestine tissue, or cervical tissue.

28. The apparatus of claim 21, wherein said at least one parameter of said intact human tissue is an indicator of a disease state.

29. The apparatus of claim 21, wherein said at least one optical parameter is indicative of a disease state, wherein said disease state is selected from the group consisting of diabetic state, vascular disease state, dermatological disease state, and neoplasmic disease state.

30. The apparatus of claim 21, wherein said irradiation means and said temperature changing means are included in an endoscope.

* * * * *